United States Patent
Yang et al.

(10) Patent No.: US 10,543,285 B2
(45) Date of Patent: Jan. 28, 2020

(54) COMPOSITIONS AND METHODS FOR TARGETED DELIVERY OF THERAPEUTIC AND/OR DIAGNOSTIC AGENTS

(71) Applicant: THE PENN STATE RESEARCH FOUNDATION, University Park, PA (US)

(72) Inventors: Jian Yang, State College, PA (US); Cheng Dong, State College, PA (US); Zhiwei Xie, State College, PA (US)

(73) Assignee: The Penn State Researh Foundation, University Park, PA (US)

(*) Notice: Subject to any disclaimer, the term of this patent is extended or adjusted under 35 U.S.C. 154(b) by 0 days.

(21) Appl. No.: 16/089,824

(22) PCT Filed: Apr. 13, 2017

(86) PCT No.: PCT/US2017/027331
§ 371 (c)(1),
(2) Date: Sep. 28, 2018

(87) PCT Pub. No.: WO2017/180820
PCT Pub. Date: Oct. 19, 2014

(65) Prior Publication Data
US 2019/0054183 A1     Feb. 21, 2019

Related U.S. Application Data

(60) Provisional application No. 62/322,927, filed on Apr. 15, 2016.

(51) Int. Cl.
*A61K 9/00*     (2006.01)
*A61K 47/69*     (2017.01)
(Continued)

(52) U.S. Cl.
CPC ........ *A61K 47/6901* (2017.08); *A61K 31/437* (2013.01); *A61K 47/593* (2017.08);
(Continued)

(58) Field of Classification Search
CPC .................................................. A61K 47/6901
See application file for complete search history.

(56) References Cited

U.S. PATENT DOCUMENTS 9,109,203 B2    8/2015   Yung et al.
2014/0017170 A1    1/2014   Irvine et al.
(Continued)

FOREIGN PATENT DOCUMENTS

WO     2012006359 A1     1/2012

OTHER PUBLICATIONS

Esposito, C et al. Multifunctional Anti-Cancer Nano-Piatforms are Moving to Clinical Trials. 61 Current Drug Metabolism, vol. 14, 2013, pp. 583-604.
(Continued)

*Primary Examiner* — Paul W Dickinson
(74) *Attorney, Agent, or Firm* — Christopher S. Dodson; Nexsen Pruet PLLC

(57) ABSTRACT

In one aspect, methods of targeted nanoparticle and cell delivery are described herein. In some embodiments, methods described herein comprise coupling nanoparticles and cells to a carrier cell to form a nanoparticle-cell conjugate or cell-cell conjugate, disposing the nanoparticle-cell or cell-cell conjugate in a biological environment, and delivering the nanoparticles and cells to target cells or tissues located within the biological environment. The nanoparticles comprise a biodegradable photoluminescent polymer, and the nanoparticle-cell conjugate is formed using one or more click chemistry reaction products.

20 Claims, 26 Drawing Sheets

(51) Int. Cl.
   *A61K 31/437* (2006.01)
   *A61K 47/65* (2017.01)
   *A61K 47/59* (2017.01)
   *A61P 35/00* (2006.01)

(52) U.S. Cl.
   CPC .......... *A61K 47/65* (2017.08); *A61K 47/6937* (2017.08); *A61P 35/00* (2018.01)

(56) References Cited

U.S. PATENT DOCUMENTS

2015/0306240 A1   10/2015  Yurkovetskiy
2016/0137776 A1*  5/2016  Yang .................... C08G 63/914
                                                        424/497

OTHER PUBLICATIONS

Chellat, Fetal. Metalloproteinase and cytokine production by THP-1 macrophages following 67 exposure to chitosan-DNA nanoparticles. Biomaterials vol. 26, 2005, pp. 961-970.

International Search Report and Written Opinion conducted by the ISA/US and corresponding to International Application No. PCT/US2017/027331, dated Aug. 15, 2017, 20 pages.

* cited by examiner

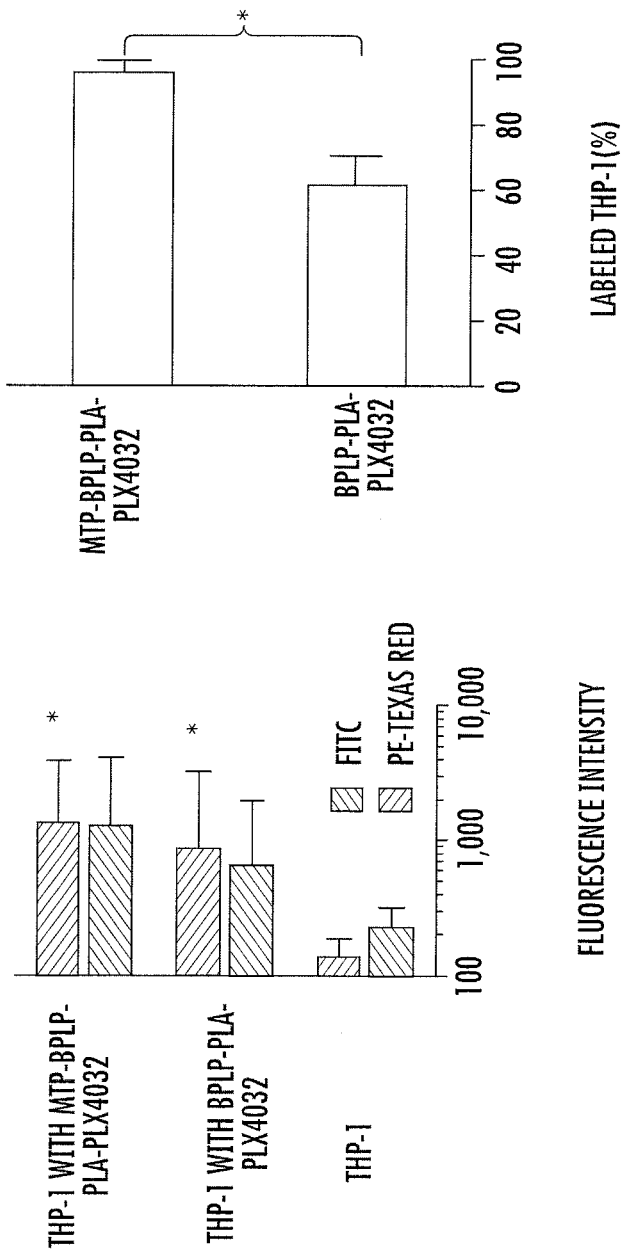

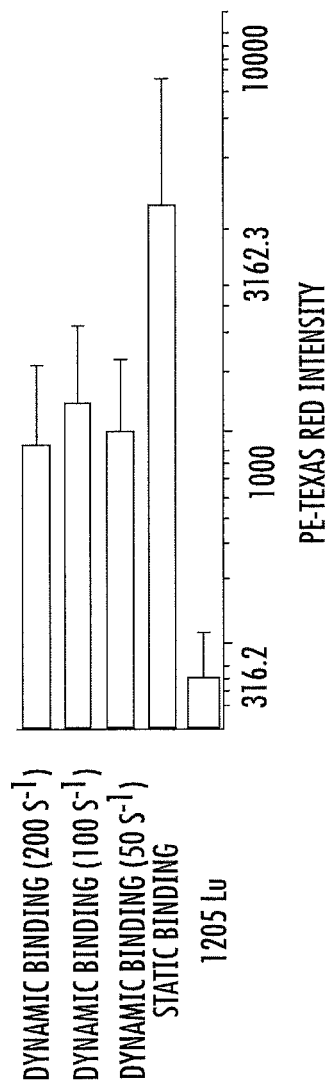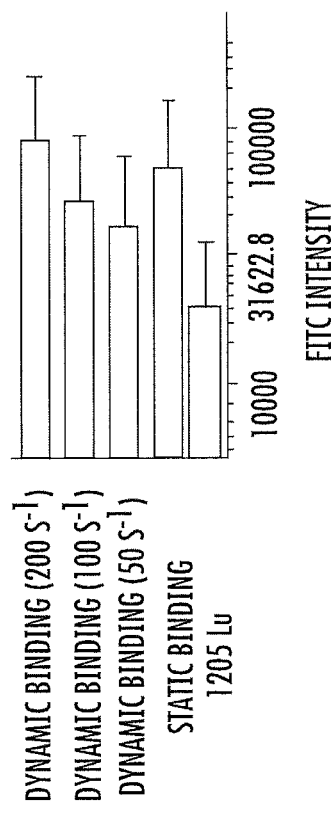
FIG. 6A
FIG. 6B

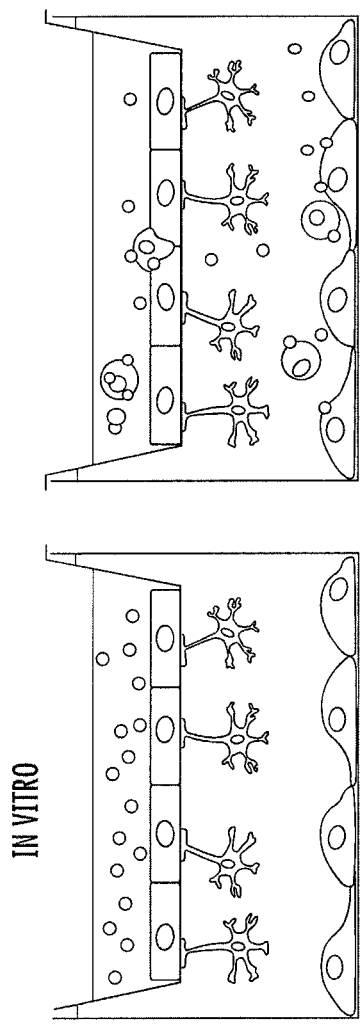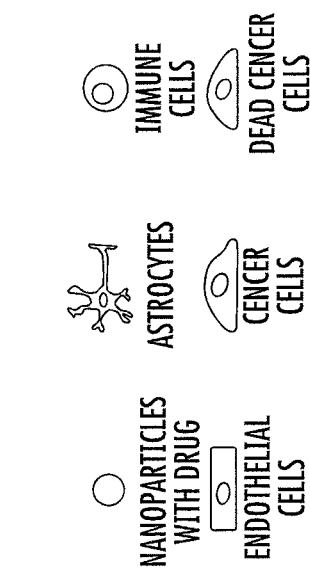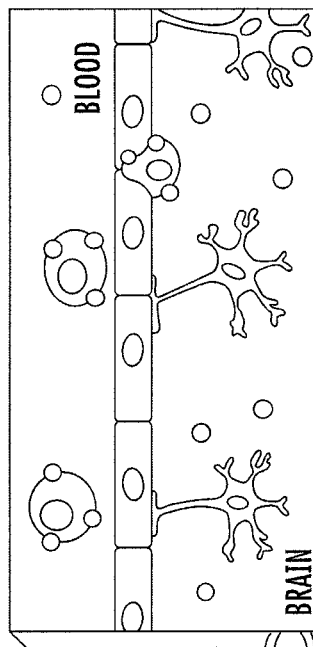
FIG. 24

COMPOSITIONS AND METHODS FOR TARGETED DELIVERY OF THERAPEUTIC AND/OR DIAGNOSTIC AGENTS

CROSS REFERENCE TO RELATED APPLICATIONS

This application is the national stage application under 35 U.S.C. § 371 of International Application No. PCT/US2017/027331, filed Apr. 13, 2017, which claims priority pursuant to 35 U.S.C. § 119(e) to U.S. Provisional Patent Application Ser. No. 62/322,927, filed Apr. 15, 2016, each of which is hereby incorporated by reference in its entirety.

STATEMENT REGARDING FEDERALLY SPONSORED RESEARCH

This invention was made with government support under Grant No. EB012575, awarded by the National Science Foundation and under Grant No. DMR1313553, awarded by the National Science Foundation. The Government has certain rights in the invention.

FIELD

This invention relates to cell mediated drug delivery and cell tracking and, in particular, to compositions and methods for accomplishing the same.

BACKGROUND

Numerous materials and methods have been developed to provide spatial and temporal control of the delivery of cells and drugs for localized therapy. For example, in cancer management, nanoparticles derived from either synthetic materials or natural materials can be used as vehicles to carry therapeutic drugs, genes, and imaging agents [Reference 1 below]. The nanoparticles are usually "decorated" with targeting ligands or molecules such as peptides, antibodies, aptamers, and proteins that are specific to the receptors expressed or overexpressed on the cancer cells [References 2, 3]. Such payload-bearing nanoparticles are called "stealthy vehicles" or "Trojan horses" as they can be injected into the circulation and accumulate into the tumors through a passive targeting mechanism, namely enhanced permeation and retention (EPR) caused by the leaky vasculature and the malfunctioned lymphatic drainage in tumors, and/or an active targeting mechanism via the guidance of cancer-specific ligands or molecules [References 4, 5]. Unfortunately, despite significant progress in the discovery of surface markers, targeting ligands and molecules, and biomaterial carriers, very few nanoparticles are truly specific after intravenous injection, and the targeting remains essentially chance-dependent, which results in a wide bio-distribution of nanoparticles (and their payloads) throughout the body, thus causing significant side effects [References 2, 6, 7]. Realizing truly specific "live" or "smart" targeting for effective drug delivery in cancer management remains a significant challenge.

SUMMARY

Compositions and methods are described herein which overcome one or more of the deficiencies of prior compositions and methods to address the foregoing concerns. For example, in some embodiments, compositions and methods described herein provide targeted delivery of therapeutic and/or diagnostic agents with minimal cytotoxicity. Further, in some embodiments, compositions and methods described herein can permit targeted delivery of therapeutic and/or diagnostic agents to circulating cells, such as circulating tumor or cancer cells.

In one aspect, compositions are described herein. In some embodiments, a composition described herein comprises a nanoparticle coupled to a cell to form a nanoparticle-cell conjugate. The nanoparticle comprises at least one of a therapeutic agent and a biodegradable photoluminescent polymer (BPLP). The therapeutic agent can be, for example, a drug, a stem cell, or a T-cell. In other cases, a composition described herein comprises an enzyme-sensitive degradable peptide comprising a first clickable moiety or a pH sensitive degradable polymer comprising a first clickable moiety, and a therapeutic agent or therapeutic agent-containing nanoparticle conjugated, e.g., via a covalent bond, to the enzyme-sensitive degradable peptide comprising a first clickable moiety or the pH sensitive degradable polymer comprising a first clickable moiety. In some embodiments, the first clickable moiety of the enzyme degradable peptide or of the pH sensitive polymer reacts with a second clickable moiety on a surface of a cell, via a click chemistry reaction, to form a nanoparticle-cell conjugate, e.g., a therapeutic agent-cell conjugate or a therapeutic agent-containing nanoparticle-cell conjugate.

In still other instances, a composition described herein comprises a stem cell, a linker, and an immune cell, wherein the stem cell is coupled to the linker, e.g., a peptide, and the linker is coupled to the immune cell to form a stem cell-peptide-immune cell conjugate. Such compositions are described in further detail hereinbelow.

In another aspect, methods of targeted nanoparticle delivery are described herein. Some such methods can comprise coupling nanoparticles to carrier cells to form nanoparticle-cell conjugates, disposing the nanoparticle-cell conjugates in a biological environment, and delivering the nanoparticles to target cells located within the biological environment. The nanoparticles can comprise a biodegradable photoluminescent polymer (BPLP).

In yet another aspect, methods of targeted therapeutic agent delivery are described herein. In some embodiments, such a method comprises providing a composition described hereinabove to a biological environment containing target cells. For instance, in some cases, a method described herein comprises forming a therapeutic agent-containing nanoparticle-cell conjugate by reacting a first clickable moiety of an enzyme-degradable peptide or of a pH sensitive polymer with a second clickable moiety on a surface of a carrier cell, via a click chemistry reaction. The method further comprises disposing the nanoparticle-cell conjugate in a biological environment. The biological environment comprises a target cell and the environment and/or the target cell degrades the enzyme-sensitive degradable peptide or the pH sensitive degradable polymer, resulting in release of the therapeutic agent of the nanoparticle-cell conjugate.

In a further aspect, methods of targeted stem cell delivery are described herein. In some embodiments, such a method comprises providing a composition comprising a stem cell linked to an immune cell, such as described above. The method further comprises disposing the composition in a biological environment, and coupling the stem cell to a target tissue through an interaction between the immune cell and the target tissue.

These and other embodiments are described in more detail in the detailed description that follows.

BRIEF DESCRIPTION OF THE DRAWINGS

FIG. 5A is a graph showing FITC and PE-Texas Red average fluorescence intensity of THP-1 cells labeled by nanoparticles according to some embodiments described herein.

FIG. 5B is a graph showing binding efficiency of nanoparticles according to some embodiments described herein.

FIGS. 6A and 6B are Average fluorescence intensity of PE-Texas Red and FITC within the Q1 and Q2 areas of FACS analysis of embodiments described herein.

FIG. 24 is a schematic showing use of cell-nanoparticle conjugates according to some embodiments described herein.

DETAILED DESCRIPTION

Figure 1:
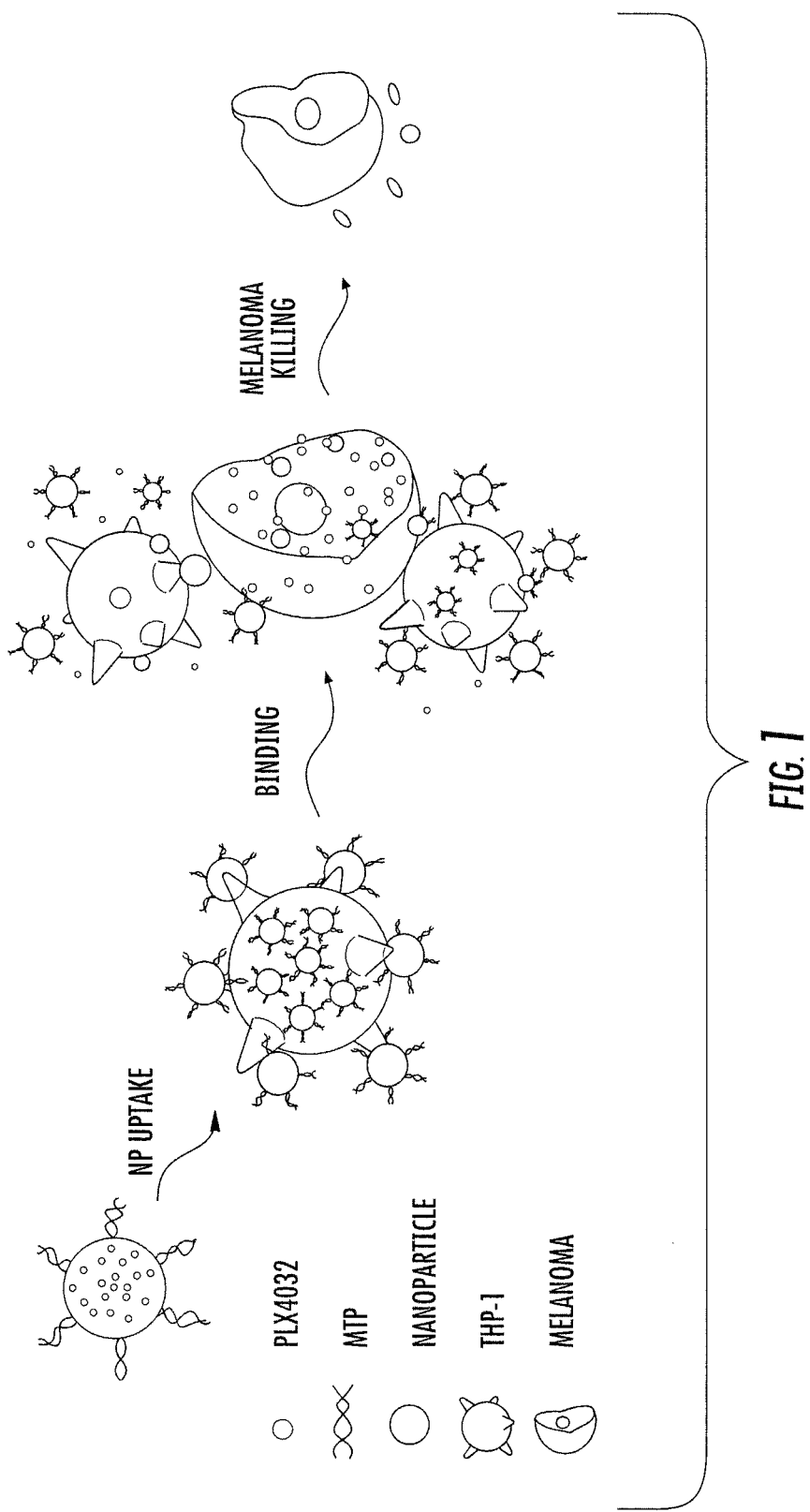
FIG. 1 is a schematic illustration of an immune cell-mediated nanoparticle delivery method according to some embodiments described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the end points 5 and 10. Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Methods of Targeted Nanoparticle Delivery and Compositions for the Same

In one aspect, compositions are described herein. In some embodiments, a composition described herein comprises a nanoparticle coupled to a cell to form a nanoparticle-cell conjugate. Specific components of such nanoparticle-cell conjugates will now be described in more detail. The nanoparticle of a nanoparticle-cell conjugate can comprise or be any nanoparticle not inconsistent with the objectives of the present invention. In some cases, the nanoparticle comprises, consists of, or consists essentially of at least one of a therapeutic agent, e.g., a drug, a stem cell, or a white blood cell (e.g., a T-cell), and a biodegradable photoluminescent polymer (BPLP), as described further below.

Additionally, the nanoparticle may have a diameter or size in at least one dimension of 300 nm or less, 250 nm or less, 200 nm or less, or 150 nm or less. In some instances, the nanoparticle has such a diameter or size in two dimensions or three dimensions. Moreover, in some embodiments, the nanoparticle has a negative zeta potential, including a large negative zeta potential. For instance, in some embodiments, the negative zeta potential has an absolute value of at least 10 mV, at least 20 mV, or at least 30 mV. In some cases, the nanoparticle has a zeta potential of −10 mV to −60 mV, −10 mV to −40 mV, or −20 mV to −40 mV. Further, in some embodiments, a population of nanoparticles described herein has a polydispersity index (PDI) ranging from 0.10 to 0.20, 0.12 to 0.19, 0.13 to 0.17, or 0.12 to 0.15.

Turning again to nanoparticles formed from a BPLP, any biodegradable photoluminescent polymer (BPLP) not inconsistent with the present invention can be used. A biodegradable polymer, for reference purposes herein, degrades in vivo to non-toxic components that can be cleared from the body by ordinary biological processes. In some embodiments, a biodegradable polymer completely or substantially completely degrades in vivo over the course of about 90 days or less, about 60 days or less, or about 30 days or less, where the extent of degradation is based on percent mass loss of the biodegradable polymer, and wherein complete degradation corresponds to 100% mass loss. Specifically, the mass loss is calculated by comparing the initial weight ($W_0$) of the polymer with the weight measured at a pre-determined time point ($W_t$) (such as 30 days), as shown in equation (1):

$$\text{Mass loss (\%)} = \frac{(W_0 - W_t)}{W_0} \times 100. \qquad (1)$$

Similarly, it is to be understood that the term "photoluminescent" includes fluorescent and/or phosphorescent polymers or oligomers. Moreover, it is to be understood that the term photoluminescent is not intended to be limiting of the nature, characterization, or nomenclature of the light emission process of the photoluminescent compositions. Moreover, a luminescent or fluorescent polymer or oligomer described herein, in some instances, can exhibit a luminescence or fluorescence emission profile centered in the visible or near infrared (NIR) region of the electromagnetic spectrum. For example, in some embodiments, a luminescent or fluorescent polymer or oligomer described herein, in some instances, exhibits a luminescence or fluorescence emission profile centered at a wavelength between about 390 nm and about 725 nm, between about 430 nm and about 650 nm, or between about 500 nm and about 700 nm. Moreover, in some implementations, a luminescent or fluorescent polymer or oligomer described herein resists photobleaching and/or has superior photobleaching characteristics compared to some other organic dyes. Methods described herein can further comprise imaging the biological environment at one or more time points using the BPLP (including using photoluminescence of the BPLP).

In some embodiments, the BPLP comprises a polymer or oligomer formed from the reaction product of (i) a polycarboxylic acid or a polycarboxylic acid equivalent, (ii) a polyol, and (iii) an amino acid or primary amine.

In some such embodiments, the polycarboxylic acid or polycarboxylic acid equivalent comprises a citric acid, a citrate, or an ester of citric acid. In some cases, a polycarboxylic acid or polycarboxylic acid equivalent described herein comprises one or more additional moieties operable to form a linkage with an amino acid described herein. For example, in some instances, a polycarboxylic acid or polycarboxylic acid equivalent comprises a hydroxyl moiety. Moreover, in some implementations, the additional moiety, such as an additional hydroxyl moiety, is geminal to a carboxylic acid functional group of the polycarboxylic acid or polycarboxylic acid equivalent. In some embodiments, a polycarboxylic acid or polycarboxylic acid equivalent comprises citric acid, a citrate, or an ester of citric acid, such as triethyl citrate or another methyl or ethyl ester of citric acid.

Moreover, a polycarboxylic acid or functional equivalent thereof can be saturated or unsaturated. For example, in some instances, a polycarboxylic acid or polycarboxylic acid equivalent comprises maleic acid, maleic anhydride, fumaric acid, or fumaryl chloride. A vinyl- or allyl-containing polycarboxylic acid or polycarboxylic acid equivalent may also be used, such as allylmalonic acid, allylmalonic chloride, itaconic acid, or itaconic chloride. Further, in some cases, a polycarboxylic acid or polycarboxylic acid equivalent can be partially replaced with an olefin-containing monomer that may or may not be a polycarboxylic acid. In some embodiments, for instance, an olefin-containing monomer comprises an unsaturated polyol such as a vinyl-containing diol. In some embodiments, a polycarboxylic acid or polycarboxylic acid equivalent comprises citric acid, a citrate, or an ester of citric acid, such as triethyl citrate or another methyl or ethyl ester of citric acid.

Any polyol not inconsistent with the objectives of the present disclosure may be used to form the BPLP polymer or oligomerdescribed herein. In some cases, for instance, a polyol comprises a diol. A diol, in some embodiments, is a macrodiol. A "macrodiol," for reference purposes herein, comprises a polymer or oligomer comprising terminal hydroxyl groups. For example, in some embodiments, a macrodiol can be a poly(lactic acid) or another hydrophobic polymer or oligomer functionalized or derivatized to be a diol. Further, in some instances, a polyol comprises a poly(ethylene glycol) (PEG) or poly(propylene glycol) (PPG). Any PEG or PPG not inconsistent with the objectives of the present disclosure may be used. In some embodiments, for instance, a PEG or PPG has a weight average molecular weight between about 100 and about 5000 or between about 200 and about 1000.

In other embodiments, a polyol is a small molecule diol such as a diol comprising from about 8 to about 30 carbon atoms (which can also be referred to as a C8-C30 diol). A C8-C30 diol can be linear or branched, aliphatic or aromatic. Non-limiting examples of polyols suitable for use in some embodiments described herein include C2-C20, C2-C12, or C2-C6 aliphatic alkane diols, including α,ω-n-alkane diols, or α,ω-alkene diols. For instance, in some cases, a polyol comprises 1,4-butanediol, 1,6-hexanediol, 1,8-octanediol, 1,10-decanediol, 1,12-dodecanediol, 1,16-hexadecanediol, or 1,20-icosanediol. Branched α,ω-alkane diols or α,ω-alkene diols can also be used. Additionally, a polyol can also be an aromatic diol.

An amino can comprise any amino acid not inconsistent with the objectives of the present disclosure. In some embodiments, an amino acid comprises an alpha-amino acid. Further, an alpha-amino acid of a polymer or oligomer described herein, in some cases, comprises an L-amino acid, a D-amino acid, or a D,L-amino acid. such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine, or a combination thereof. Moreover, in some instances, an alpha-amino acid comprises an alkyl ester amino acid, an aryl ester amino acid, or an alkyl-substituted alpha-amino acid, such as a methyl-substituted amino acid derived from any of the 22 "standard" or proteinogenic amino acids, such as S-benzyl-L-cysteine, S-phenyl-S-cysteine, tryptophan benzyl ester, S-methyl-cysteine, L-histidine methyl ester, phenylalanine methyl ester, L-tyrosine methyl ester, 1-methyl-L-histidine, 1-methyl-D-tryptophan, 1-methyl-L-tryptophan, or methyl serine. An amino acid may also be a non-naturally occurring amino acid or amino acid derivative.

A primary amine can comprise any primary amine not inconsistent with the objectives of the present disclosure. In some embodiments, a primary amine including one of natural and synthetic amino acids, amino thiols, monoamines, diamines, and triamines, may be used.

Moreover, in some cases, a BPLP described herein comprises or is a block copolymer. In some such instances, the block copolymer comprises a first block comprising or formed form a polymer or oligomer described in the preceding paragraphs (e.g., a polymer or oligomer formed from the reaction product of (i) a polycarboxylic acid or a polycarboxylic acid equivalent, (ii) a polyol, and (iii) an amino acid or primary amine). Such a block of the block copolymer can exhibit luminescence or fluorescence.

Such a block copolymer described herein can further comprise a second block comprising or formed from a polymer or oligomer that differs from the polymer or oligomer of the first block. Any polymer or oligomer not inconsistent with the objectives of the present invention may be used as the second block of a block copolymer described herein. For example, in some cases, the polymer or oligomer of the second block comprises a polylactone. In some embodiments, the polymer or oligomer of the second block comprises poly-DL-lactide, poly-D-lactide, poly-L-lactide, a polyglycolide, a polycaprolactone, or a mixture or copolymer of one or more of the foregoing.

Additionally, the cell of a nanoparticle-cell conjugate described herein can be any cell not inconsistent with the objectives of the present disclosure. For instance, in some cases, the cell is selected from the group consisting of a monocyte, a macrophage, a T-cell, a B-cell, an immune cell, a lymphocyte, and a red blood cell. In some cases, the cell is a monocyte or a macrophage, such as a THP-1 cell. Moreover, a nanoparticle described hereinabove can be coupled to a cell described hereinabove in any manner not inconsistent with the objectives of the present disclosure, including in a manner described further hereinbelow in the context of carrier cells coupled to nanoparticles.

In another aspect, methods of targeted nanoparticle delivery are described herein, including using compositions described hereinabove. In some embodiments, methods described herein comprise coupling nanoparticles (including those described hereinabove) to carrier cells to form a nanoparticle-cell conjugate, disposing the nanoparticle-cell conjugate in a biological environment, and delivering the nanoparticles to target cells located within the biological environment. In some cases, the nanoparticles comprise, consist of, or consist essentially of at least one of a therapeutic agent, e.g., a drug, a stem cell, or a white blood cell (e.g., a T-cell), and a biodegradable photoluminescent polymer. Any biodegradable photoluminescent polymer can be used consistent with the above description of BPLPs. Additionally, in some embodiments, individual nanoparticles have an uptake agent attached to the outer surface of the nanoparticles. An uptake agent can increase the cellular uptake efficiency of the nanoparticle. In some embodiments, the uptake agent is muramyl tripeptide (MTP) or muramyl dipeptide (MDP) (see FIG. 5A and FIG. 5B). Other uptake agents may also be used, such as R-11 peptide or other cell penetrating peptides or molecules.

In some embodiments, methods described herein further comprise disposing a therapeutic agent within the nanoparticles (e.g., nanoparticles comprising or formed from a BPLP), prior to delivering the nanoparticles to the target cells, and/or prior to coupling the nanoparticles to a carrier cell. In some cases, methods described herein also comprise delivering the therapeutic agent to the target cells. Any therapeutic agent not inconsistent with the present invention can be used. For example, in some embodiments, the therapeutic agent is a targeted enzyme inhibitor, such as PLX4032. In certain other embodiments, the therapeutic agent is a cytotoxic agent, such as a targeted cytotoxic agent. A therapeutic agent may also be an anti-cancer drug. For example, the cytotoxic agent can be Docetaxel, Cytoxan, Imuran, Methotrexate, and/or Pacilitaxel.

Any carrier cell not inconsistent with the objectives of the present invention can be used in a method described herein. For example, in some embodiments, the carrier cell is selected from the group consisting of a monocyte, a macrophage, a T-cell, a B-cell, an immune cell, a lymphocyte, and a red blood cell. In some cases, the carrier cell is a monocyte or a macrophage, such as a THP-1 cell. Further, any target cell can be used not inconsistent with the objectives of the present invention. For example, in some cases, the target cells are cancer cells, such as melanoma cells or brain tumor cells. Additionally, in some embodiments, the cancer cells are circulating tumor cells. In some embodiments, the biological environment is a blood stream or a blood vessel of a living organism. In some embodiments, the biological environment is in the brain of a living organism, and the nanoparticle-cell conjugate is operable to cross the blood-brain barrier.

The nanoparticles used in methods described herein can be coupled to the carrier cells, to form a nanoparticle-cell conjugate, in any manner not inconsistent with the objectives of the present invention. For example, in some embodiments, the nanoparticles are coupled to the carrier cells by phagocytosis of the nanoparticles by the carrier cells, such as may be accomplished by incubating the nanoparticles with the carrier cells in an appropriate medium such as a buffered medium. In certain other embodiments, the nanoparticles are coupled to the carrier cells by a click-chemistry reaction as described further herein below in which a first clickable moiety of the nanoparticle is reacted with a second clickable moiety on the external surface of the carrier cell.

In some embodiments, one or more components of a composition combines, connects, or couples to another component or cell through a click chemistry reaction scheme. In some cases, for example, a composition described herein comprises one or more alkyne moieties or one or more azide moieties that may react in the click chemistry reaction scheme. A second component intended to be coupled to the first component can comprise one or more alkyne moieties or one or more azide moieties, with the selection of the use of an alkyne or azide moiety differing between the first and second components. For example, a nanoparticle coupled to a carrier cell by click chemistry, to form a nanoparticle-cell conjugate, may comprise a nanoparticle having an alkyne moiety on an exterior surface being coupled to a carrier cell having an azide moiety on an exterior surface. The alkyne and azide moieties would react to couple the nanoparticle and the carrier cell.

It is also possible to couple two or more components using a click chemistry reaction scheme that does not necessarily form azide-alkyne cycloaddition products. For instance, in some cases, one or more monomers comprising an alkyne and/or azide moiety described herein can be at least partially replaced by one or more monomers comprising a different moiety that can participate in a click chemistry reaction scheme. For example, in some embodiments, a coupling is formed from the reaction of one or more monomers comprising a thiol moiety with one or more monomers comprising an alkene (or alkyne) moiety through a thiol-ene/yne click reaction. Such a thiol-ene/yne click reaction can comprise the addition of an S—H bond across a carbon-carbon double bond or triple bond by a free radical or ionic mechanism. Any click chemistry reaction not inconsistent with the objectives of the present disclosure may be used. In some instances, the click chemistry reaction comprises a [3+2] cycloaddition such as a Huisgen alkyne-azide cycloaddition; a thiol-ene/yne reaction; a Diels-Alder reaction; an inverse electron demand Diels-Alder reaction; a [4+1] cycloaddition such as the cycloaddition reaction of an isocyanide with a tetrazine; or a nucleophilic substitution reaction involving a strained ring such as an epoxy or aziridine ring.

II. Compositions and Methods for Targeted Therapeutic and Stem Cell Delivery

In another aspect, compositions are described herein that may be used in methods for targeted therapeutic agent delivery. In some embodiments, compositions described herein comprise an enzyme-sensitive degradable peptide comprising a first clickable moiety and a therapeutic agent or therapeutic agent-containing nanoparticle conjugated to the enzyme-sensitive degradable peptide and/or the compositions may comprise a pH-sensitive degradable polymer comprising a first clickable moiety and a therapeutic agent or therapeutic-agent containing nanoparticle conjugated to the pH sensitive degradable polymer. Any clickable moiety (e.g., an alkyne) and/or click chemistry reaction consistent with the above discussion in Section I can be used. In some embodiments, an enzyme-sensitive peptide is any peptide that binds to and undergoes a reaction, e.g., is cleaved, at an enzyme's active site. In some cases, the enzyme may be an enzyme that is present in elevated amounts in cancerous tissues, e.g., Matrix metalloproteinases (MMPS), CPE, PAM, and PC1/3 plus PC2, In some cases, the pH sensitive polymer is one that is cleavable, e.g., by hydrolyzing, at a particular pH. In some embodiments, the pH sensitive polymer comprises a group or moiety that is stable at neutral pH, but can be broken or cleaved, e.g., by undergoing hydrolysis, at acidic pH. In some embodiments, the pH sensitive polymer can comprise a hydrazone-based bonds, cis-acotinyl bonds, and acetal bonds [Reference 46].

The above-described therapeutic agent or therapeutic agent-containing nanoparticle conjugated to an enzyme-sensitive degradable peptide comprising a first clickable moiety (or the therapeutic agent or therapeutic-agent containing nanoparticle conjugated to the pH sensitive degradable polymer comprising a first clickable moiety) may be conjugated to a carrier cell, e.g., an immune cell, having a second clickable moiety on the surface thereof. A cell-nanoparticle conjugate may be formed via a click chemistry reaction between the first clickable moiety and the second clickable moiety.

Similarly, methods of targeted therapeutic agent delivery are described herein. Such methods can comprise providing the foregoing composition comprising an enzyme-sensitive degradable peptide and/or a pH sensitive degradable polymer and disposing the composition in a biological environment, including a biological environment comprising a target cell or a population or plurality of target cells. In some embodiments, the biological environment and/or the target cell may be such that the enzyme-sensitive degradable peptide and/or the pH sensitive degradable polymer are cleaved when exposed to the target cell and/or biological environment, resulting in targeted release of the therapeutic agent or therapeutic agent-containing particles at or near the target cells. For example, the biological environment may comprise an enzyme that can cleave or degrade the enzyme-sensitive peptide and/or the biological environment may be acidic, such that the pH sensitive polymer is cleaved.

In a further aspect, compositions are described herein that may be used in methods for targeted stem cell delivery (or other deliverable cell delivery, including white blood cells, such as T-cells). In some embodiments, compositions described herein comprise a stem cell (or other deliverable cell), a linker, and an immune cell (or other carrier cell). The stem cell (or other deliverable cell) is coupled to the linker and the linker is coupled to the immune cell (or other carrier cell) to form a stem cell (or other deliverable cell)-peptide-immune cell (or other carrier cell conjugate, e.g., a cell-cell) conjugate. In some embodiments, the linker is a degradable peptide. Further, in some embodiments, the stem cell (or other deliverable cell) is coupled to the linker by a click chemistry reaction. Thus, in some embodiments, the stem cell (or other deliverable cell) comprises an azide moiety, and the peptide comprises an alkyne moiety. Moreover, in some embodiments, the immune cell (or other carrier cell) is coupled to the linker by a click chemistry reaction. Similar to the foregoing, the peptide can comprise a second alkyne moiety, and the immune cell (or other carrier cell) can comprise an azide moiety. Other click chemistry reaction schemes or components consistent with the above discussion in Section I can also be used.

Further, methods of targeted stem cell (or other deliverable cell) delivery are described herein. Such methods can comprise providing the foregoing stem cell (or other deliverable cell) containing composition, disposing the composition in a biological environment, and coupling the composition to a target tissue by interaction between the immune cell (or other carrier cell) and the target tissue. In certain embodiments, the target tissue is cardiac tissue.

Some embodiments described herein are further illustrated in the following non-limiting examples.

EXAMPLE 1

Cancer Drug Delivery

Exemplary compositions and methods for delivering anti-cancer drugs are described below. Although tremendous efforts have been made on the targeted drug delivery system, the therapy outcome still suffers from low circulating time and limited targeting efficiency. The integration of cell-mediated drug delivery and theranostic nanomedicine can potentially improve cancer management in both therapeutic and diagnostic aspects. Herein is described a drug delivery system using macrophages both as nanocarriers and navigators to achieve cancer-specific drug delivery. Uniquely, biodegradable photoluminescent poly (lactic acid) (BPLP-PLA) was fabricated into theranostic nanoparticles, which inherently have cytocompatibility, controllable biodegradation rates and tunable fluorescence. In order to minimize the damage of carrier immune cells and other normal cells, a BRAF mutant melanoma specific drug, PLX4032, was loaded into BPLP-PLA nanoparticles. Muramyl tripeptide (MTP) was used to modify nanoparticles aimed to improve the macrophage targeting efficiency. Resulting MTP-BPLP-PLA-PLX4032 nanoparticles can be internalized by macrophages and tracked via their fluorescence. Nanoparticle-carrying macrophages were able to bind to and deliver drugs to melanoma cells both in static incubation and dynamic shear flows. Pharmaceutical studies indicated that MTP-BPLP-PLA-PLX4032 nanoparticles did not have cytotoxicity to macrophages but effectively killed melanoma cells after being delivered by macrophages.

Nanocarriers provide protection for chemotherapeutics, genes, and imaging agents, against the harsh environment during circulation. Compared to conventional systematic delivery and passive targeting, active targeting delivery of nanoparticles improves the therapeutic index and reduces the side effects and immunogenicity [References, 4, 5]. Active strategies mostly utilize surface molecules, such as antibodies, proteins, aptamers, peptides, and some small molecules, to recognize receptors that express or overexpress in cancer or cancer microenvironments [References 2, 3]. However, despite the tremendous efforts on discovering surface markers and targeting molecules, traditional nanomedicine still fails to meet the expectations of delivery therapeutics to specific tumors efficiently via intravenous injection of nanoparticles [References 2, 6]. One major challenge is that the target selectivity for a certain disease or cancer is far from ideal. The complexity in living systems makes the specific recognition chance-dependent, which compromises the effectiveness of the drug delivery systems. Thus, there is an urgent need to develop novel efficient targeting strategies for cancer nanomedicine.

Herein are described immune cell-mediated theranostic biodegradable BPLP-PLA nanoparticles for delivering melanoma specific drugs to melanoma cells. THP-1 cells, as a model for monocyte/macrophage, was selected as the particle carrier. The intrinsic fluorescence of the polymeric nanoparticles described herein enables the visualization of cell uptake and carrier cell imaging. In order to minimize the adverse effects on leukocytes and maximize the therapeutic potentials to cancer cells, PLX4032 (Vemurafenib), which is a drug specifically for BRAF mutated melanomas treatment, was selected as the therapeutic agent that is encapsulated within BPLP-PLA nanoparticles (BPLP-PLA-PLX4032) [Reference 26]. To improve the macrophages' uptake efficiency of nanoparticles, muramyl tripeptide (MTP) [Reference 27] was conjugated onto drug-loaded nanoparticles as MTP-BPLP-PLA-PLX4032. The design of nanoparticles, nanoparticle-cell conjugates, and immune-mediated targeting strategy to melanoma cells is illustrated in FIG. 1. Specifically, in FIG. 1, PLX4032 is the melanoma drug. MTP conjugated BPLP-PLA-PLX4032 nanoparticles target or conjugate to THP-1 macrophages, then the nanoparticle-cell conjugate is delivered to melanoma cells via interactions of THP-1 macrophages and melanoma cells, and eventually PLX4032 drugs are released to kill cancer cells.

Fabrication and Characterization of BPLP-PLA nanoparticles.

Figure 2B:
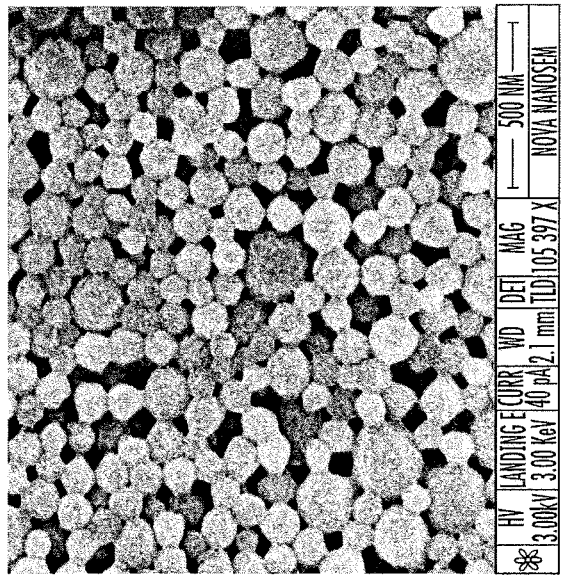
FIGS. 2A and 2B are each SEM images of nanoparticles according to some embodiments described herein.
Figure 2A:
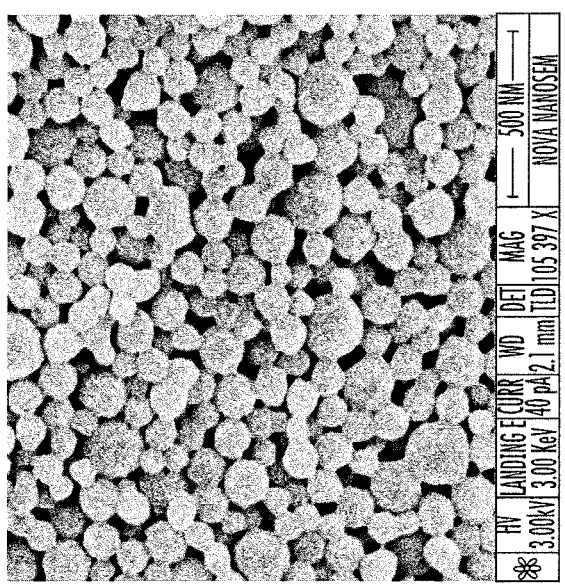
Figure 10:
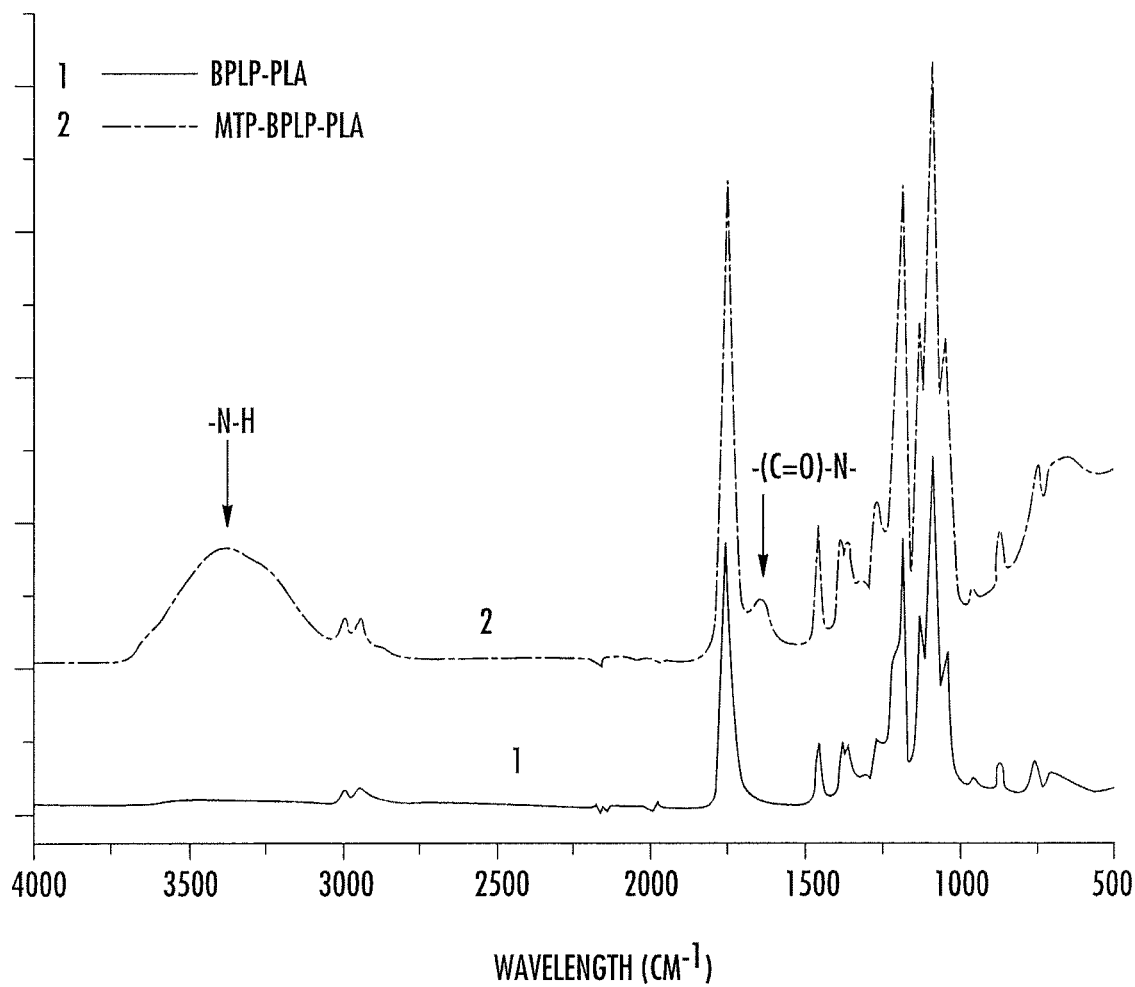
FIG. 10 illustrates FTIR spectra of nanoparticles according to some embodiments described herein.

Unlike existing immune cell mediated nanoparticle delivery systems utilizing inorganic nanoparticles and liposomes that lack theranostic potential and controlled drug release mechanism [References 20, 21, 23], biodegradable BPLP-PLA described herein was used in this study for immune cell-mediated delivery. BPLP-PLA copolymer with intrinsic fluorescence was synthesized as reported previously [Reference 25, 28]. Not intending to be bound by theory, varying the BPLP to L-lactide molar ratio, which is 1:50 in this study, is believed to permit control of the degradation rate [Reference 25]. This BPLP-PLA copolymer was selected to ensure minimal degradation and drug release in 24 hrs, which is the time window for immune cell uptake nanoparticles and further binding to melanoma cells. BPLP-PLA nanoparticles were fabricated by a single emulsion method [Reference 25, 28]. In order to increase THP-1 targeting efficiency, the drug-laden nanoparticles were further modified with MTP, which has macrophage immunopotentiating effects without any cytotoxicity [References 29-31]. MTP was successfully conjugated with BPLP-PLA and BPLP-PLA-PLX4032 nanoparticles by carbodiimide chemistry, as confirmed by FTIR (FIG. 10). The increments of —NH stretching and —(C=O)N— stretching indicate the presence of peptides on BPLP-PLA nanoparticles. Next, PLX4032 was selected as the drug for encapsulation, since it is specific for the treatment of BRAF (V600E) mutation melanoma [Reference 26]. PLX4032 encapsulated BPLP-PLA nanoparticles were fabricated by the same single emulsion method and mixing PLX4032 into BPLP-PLA with a ratio of 1:5 w/w. The drug loading efficiency was 54% as determined by HPLC. Scanning electron microscopy (SEM) images of PLX4032 loaded nanoparticles (BPLP-PLA-PLX4032) and MTP modified BPLP-PLA-PLX4032 nanoparticles (MTP-BPLP-PLA-PLX4032) are shown in FIGS. 2A and 2B with a scale bar of 500 nm. Average size, polydispersity index, and Zeta potential of both nanoparticles is reported below in Table 1:

TABLE 1

| Nanoparticles | Average Size (nm) | PDI | Zeta Potential (mV) |
|---|---|---|---|
| BPLP-PLA-PLX4032 | 217.2 | 0.147 | −30.3 |
| MTP-BPLP-PLA-PLX4032 | 209.1 | 0.121 | −36.2 |

Figure 3:
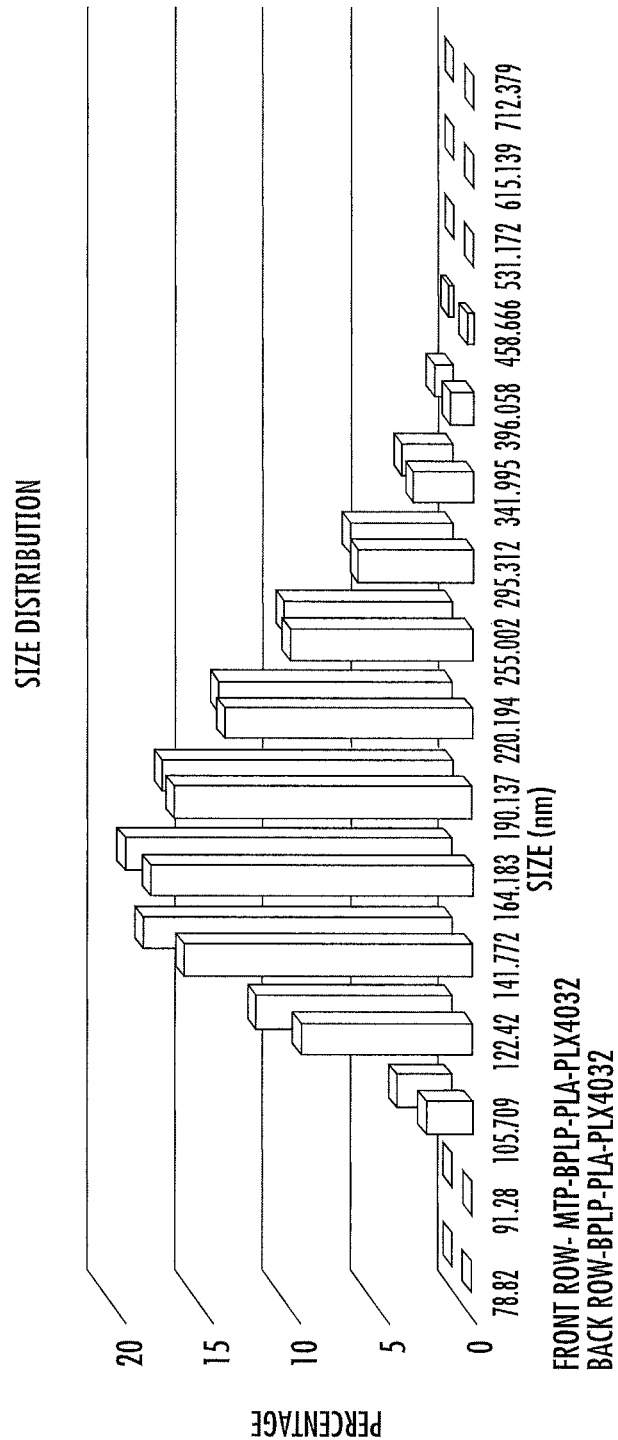
FIG. 3 is a graph showing the size distribution of populations of nanoparticles according to some embodiments described herein.
Figure 4:
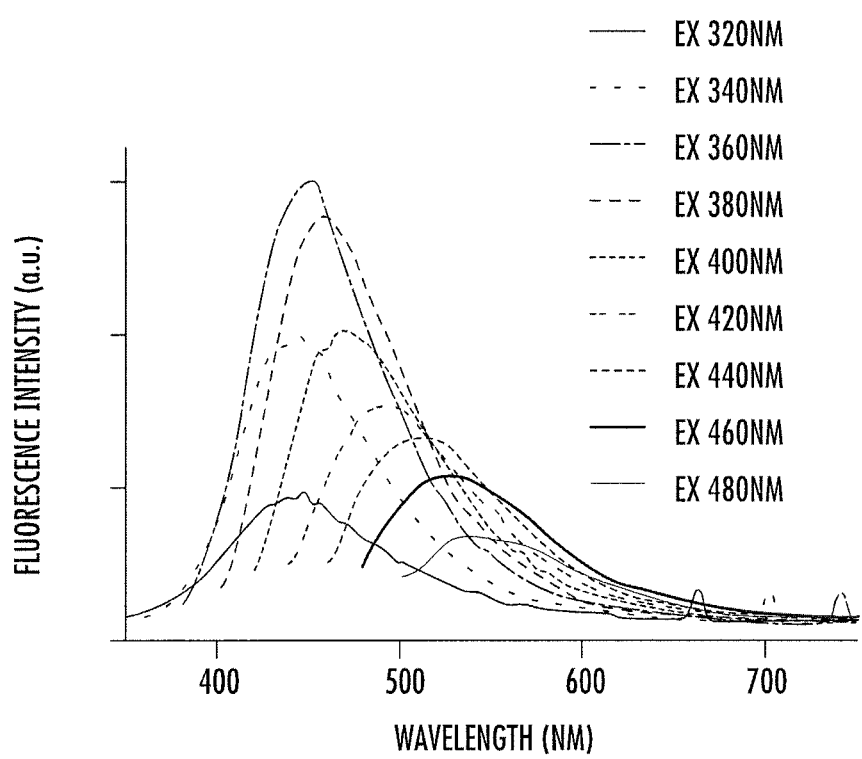
FIG. 4 illustrates fluorescence emission spectra of nanoparticles according to some embodiments described herein.

FIG. 3 shows the size distribution of both nanoparticles. The average size was determined by dynamic light scattering (DLS). The results are consistent with the observation of SEM images. Zeta potentials of the nanoparticles suggest they can be stable in physiological solutions [Reference 32]. In our previous work, we found that BPLP-PLA exhibited intrinsic fluorescence and band shifting emission with different excitation wavelengths [Reference 25, 28]. Here, our nanoparticles maintain strong fluorescence emission, which is tunable up to 700 nm by increasing the excitation wavelength (FIG. 4). FIG. 4 depicts maximum fluorescence excitation and emission spectra of MTP-BPLP-PLA-PLX4032 nanoparticles in Dulbecco's phosphate-buffered saline (DPBS) suspension (20 μg/ml). The intrinsic fluorescence of nanoparticles enables in vitro visualization without secondary labeling with traditional imaging agents such as toxic organic dyes and quantum dots. BPLP-PLA also possesses excellent photostability, which is desired for cell tracking purposes [Reference 25, 33].

THP-1 Cells Uptake Drug-Laden Nanoparticles.

Figure 12:
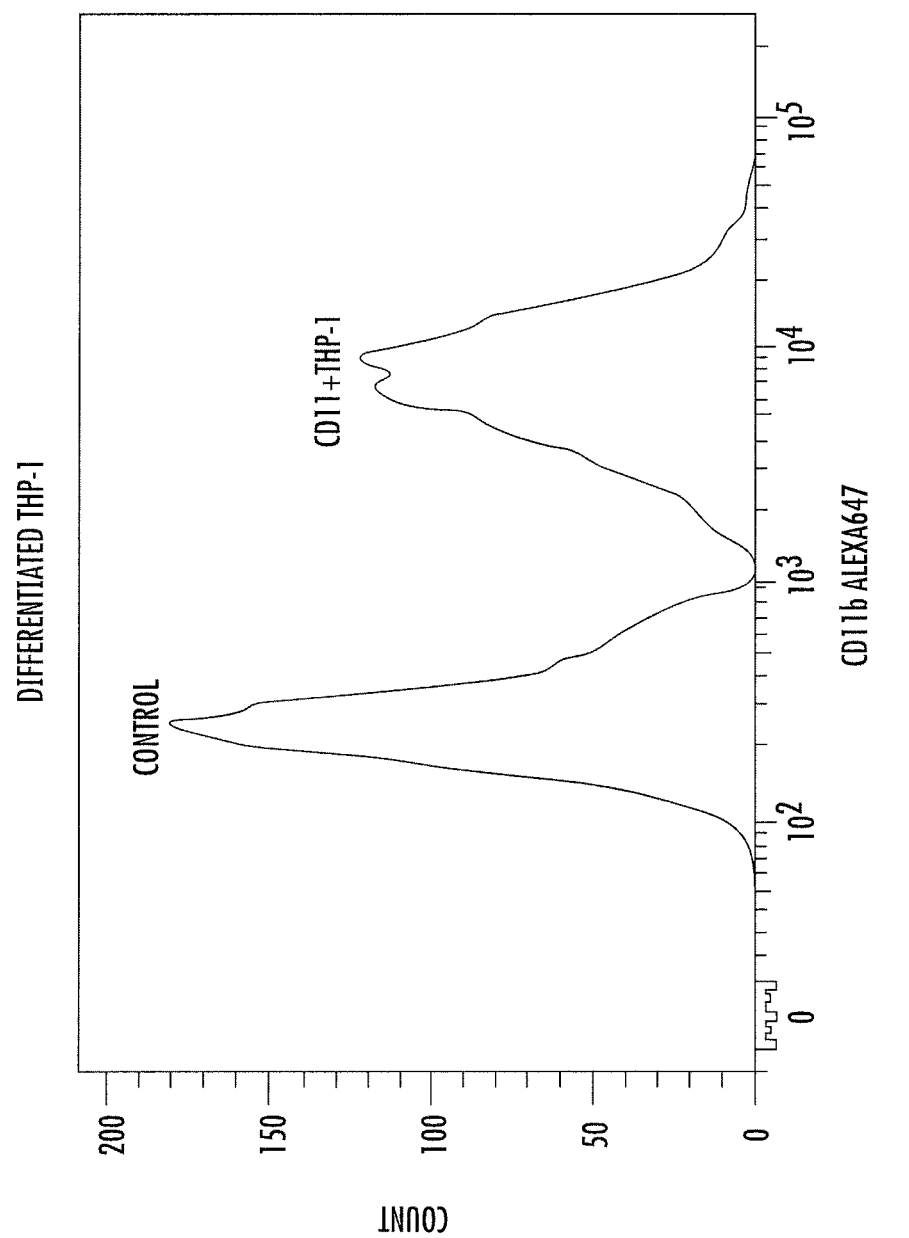
FIG. 12 illustrates CD11b expressions of differentiated THP-1 cells as the fluorescence intensity of Alexa647 measured by flow cytometry.
Figure 13:
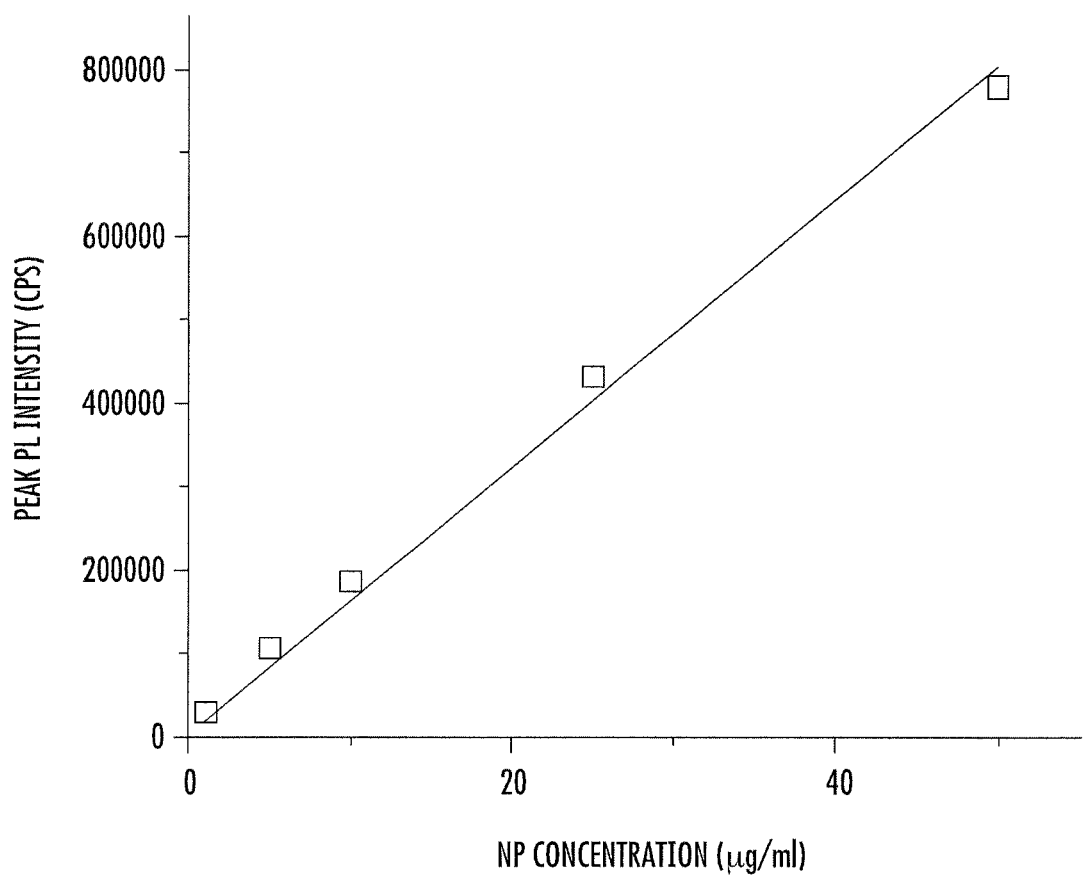
FIG. 13 is a calibration curve of peak photoluminescence intensity as a function of nanoparticle concentration for nanoparticles according to some embodiments described herein.

THP-1 is a well-established native monocyte-derived macrophage model [Reference 34]. Differentiated THP-1 cells induced by Phorbol 12-myristate 13-acetate (PMA) demonstrate macrophage like phenotype, which is confirmed by the expression of CD11b (namely MAC-1 or Integrin alpha M) (FIG. 12). BPLP-PLA-PLX4032 and MTP-conjugated BPLP-PLA-PLX4032 nanoparticles were incubated with THP-1 cells for 2 hrs on a rocker. The intrinsic fluorescence of these nanoparticles after being internalized by THP-1 can be observed in both FITC and PE-Texas Red channels by confocal microscopy. Due to the BPLP-PLA nanoparticles' band shifting behavior, the emission can be observed in both colors. Thus, these fluorescent nanoparticles enabled the visualization and tracking of THP-1 cells. The results were also confirmed by flow cytometry, as both FITC and PE-Texas Red intensity were improved after nanoparticles uptake ( ). MTP was conjugated to BPLP-PLA-PLX4032, aiming to improve the nanoparticle binding to THP-1 cells. It is clear that both FITC and PE-Texas Red fluorescence increased further with MTP conjugated nanoparticles, including more nanoparticle uptake by THP-1 cells. Quantitatively, the average FITC and PE-TEXAS RED intensity of THP-1 cells treated with MTP-BPLP-PLA-PLX4032 nanoparticles were stronger than that with BPLP-PLA-PLX4032 nanoparticles (FIG. 5A), suggesting that MTP-BPLP-PLA-PLX4032 nanoparticles can increase the THP-1 internalization and nanoparticle loading efficiency. The nanoparticle targeting efficiency was determined by the percentage of cells that have increased fluorescence in both FITC and PE-TEXAS RED channels. About 96% THP-1 cells were labeled by MTP conjugated BPLP-PLA-PLX4032 nanoparticles, compared to 61% cells that showed uptake of pristine BPLP-PLA-PLX4032 nanoparticles. (See FIG. 5B, which shows THP-1 binding efficiency as the percentage of THP-1 cells that were labeled by BPLP-PLA-PLX4032 and MTP-BPLP-PLA-PLX4032 nanoparticles, wherein *, $p<0.01$.) In terms of amount of nanoparticles added, $63.3\pm14.5\%$ of MTP conjugated nanoparticles were uptaken by THP-1 cells. This is measured based on a calibration curve of the intrinsic fluorescence from our nanoparticles (FIG. 13, which is a calibration curve of MTP-BPLP-PLA-PLX4032 nanoparticles dispersed in DPBS). Notably, THP-1 cells still expressed CD11b after internalizing the nanoparticles, suggesting that the encapsulation of the nanoparticles did not alter THP-1's functionality. From confocal microscopy images and 3D flow cytometry plots, strong immunofluorescence from Alexa647 was detected in addition to the FITC and PE-Texas Red fluorescence signals from the nanoparticles. Studies have indicated polymorphonuclear neutrophil (PMN)/melanoma cells binding through 32 integrins (e.g., CD11a/LFA-1 and CD11b/Mac-1) on PMNs and intercellular adhesion molecule-1 (ICAM-1) of melanoma cells in the blood circulation [Reference 35]. Not intending to be bound by theory, it is believed that macrophages have the same binding abilities to ICAM-1 based on the CD11b expressions on THP-1 cells [Reference 36]. Thus, the maintenance of CD11b is believed to be critical for the next step of melanoma binding. Based on these results, MTP-BPLP-PLA-PLX4032 nanoparticles were used for further melanoma binding and therapeutic studies.

THP-1 Cells Bind with Melanomas and Nanoparticles Delivery.

Figure 14:
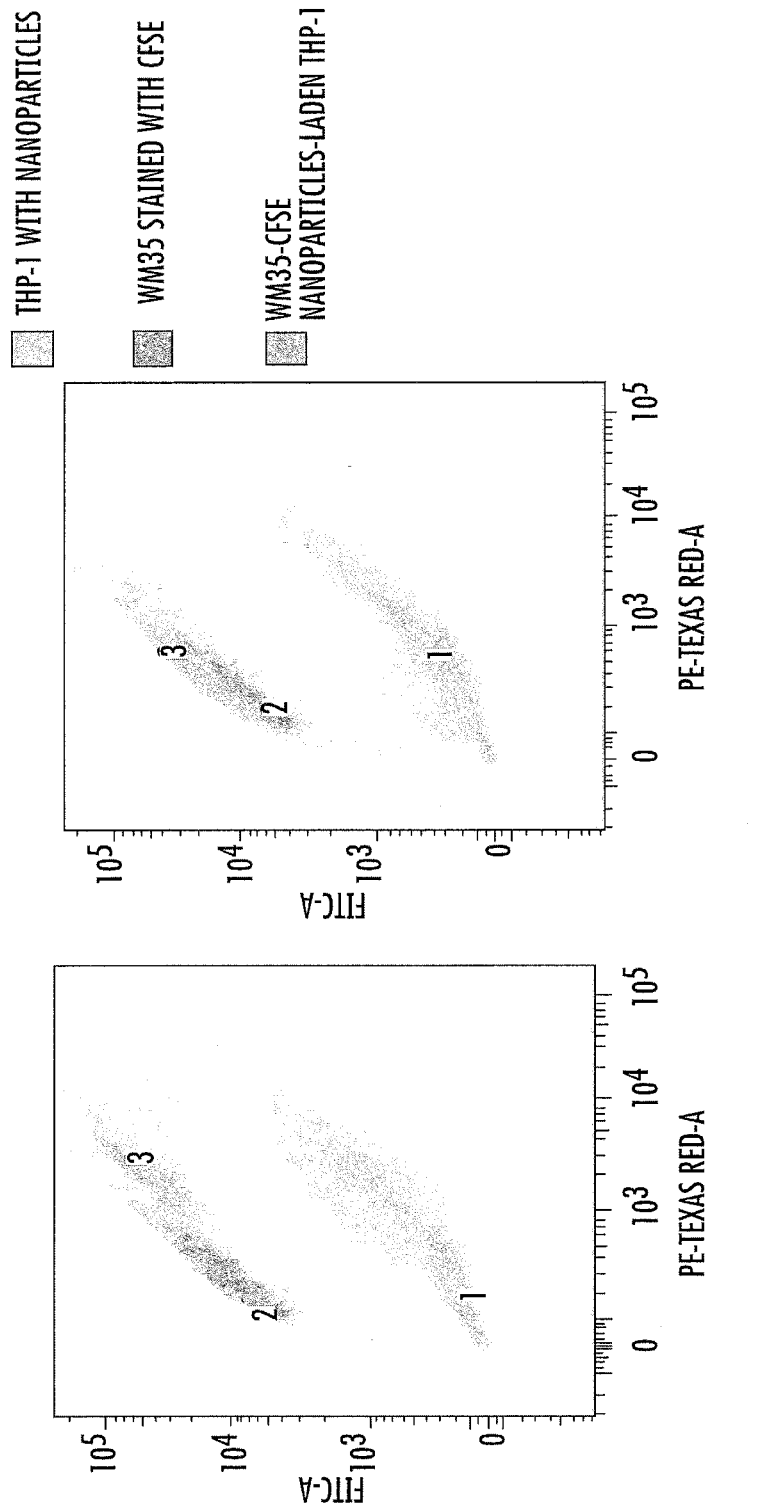
FIGS. 14A and 14B are FACS plots of cell binding in static and dynamic conditions.

Tumor progression is a complex and dynamic process involving both immune cells and tumor cells [Reference 37]. Naturally, tumor cell subpopulations are immunologically different from normal cells that are susceptible to being recognized and destroyed by immune cells. For example, macrophages are the major players in tumor microenvironment, involved in chronic inflammation, matrix remodeling, tumor cell invasion, intravasation, angiogenesis, and metastasis [Reference 38]. Herein, we report the in vitro binding between THP-1 cells and melanoma cells, as well as the nanoparticles transportation to melanomas through THP-1 cells. First, bare THP-1 cells without nanoparticles are capable of binding to melanoma cells including 1205Lu (high metastasis) and WM35 (low metastasis) under static conditions in which a mixture of macrophages and melanomas were incubated together on a rocker for 2 hours. We then examined the THP-1/melanoma binding by pre-incubating THP-1 cells with MTP-BPLP-PLA-PLX4032 nanoparticles for 2 hrs. The resulting nanoparticle-laden THP-1 cells were gently washed to remove free nanoparticles and then co-cultured with Green Fluorescent Protein-tagged 1025Lu cells (GFP-1205Lu) in static conditions. Although our nanoparticles exhibited fluorescence in both FITC and PE-Texas Red channels (FIG. 5A), the green fluorescence intensity is not as strong as the GFPlabeling. Thus, the FTIC channel was used to indicate the melanoma cells, and the PE-Texas Red channel was used to indicate the BPLP-PLA nanoparticles. After two hours incubation, it was clear that nanoparticle laden THP-1 cells bond to GFP-1205Lu, as shown in confocal microscopy images. Nanoparticle-treated THP-1 showed fluorescence in both the green and red channel, while GFP-1205Lu cells only had strong green fluorescence. To further evaluate the binding between THP1 and GFP-1205Lu, flow cytometer analysis was performed. After incubating THP-1 and GFP-1205Lu for two hours, the population of GFP-1205Lu clearly shifted to the right into the Q2 with more red fluorescence, suggesting nanoparticle bearing THP-1 cells have attached with 1205Lu cells to form leukocyte/melanoma aggregates. Interestingly, nanoparticles (PE-Texas Red fluorescence) were noted within GFP-tag 1205Lu as well, suggesting that nanoparticles were transported from THP-1 to GFP-1205Lu. Not intending to be bound by theory, it is believed that nanoparticles are released via exocytosis, owing to the equilibrium of engulfing foreign substances and liberating engulfed particles [Reference 39]. In order to mimic the dynamic shear flow environments in the bloodstream, GFP-1205Lu cells were exposed to nanoparticle-carrying THP-1 in a cone-plate viscometer. Confocal microscopy and flow cytometry results confirmed that THP-1 cells were also able to bind to GFP-1205Lu dynamic conditions. As more cells were present in Q2, both green and red fluorescence can be observed for GFP-1205Lu (FIGS. 6A and 6B). Since GFP-1205Lu has no fluorescence in the PE-Texas Red channel, significant differences were noticed after binding with nanoparticle loaded THP-1 cells in both static and dynamic experiments. Similarly, BPLP-PLA nanoparticles were observed in melanoma cells after the binding in shear flow. To quantify the THP-1/melanoma cells' binding efficiency, which is defined as the ratio of cells in Q2 over cells in both Q1 and Q2, FACS analysis was performed. Over 90% 1205Lu cells were combined with nanoparticle laden THP-1 cells with shear rates from 50 $s^{-1}$ to 200 $s^{-1}$. Again not intending to be bound by theory, these results suggest that internalization of nanoparticles did not compromise the innate capability of THP-1 to adhere with melanoma cells. In addition, THP-1 cell-mediated nanoparticle delivery was also achieved. This macrophage-mediated delivery strategy is also verified by another cell line, WM35, which is low metastasis. Similar results were observed indicating THP-1/WM35 binding and nanoparticles transportation to WM35, as shown in FIGS. 14A and 14B, which are FACS plots of cell binding after static incubation ("static") conditions and dynamic shear flow at 100 $s^{-1}$ in in cone plate viscometer ("dynamic") conditions.

Pharmaceutical Studies.

Figure 7:
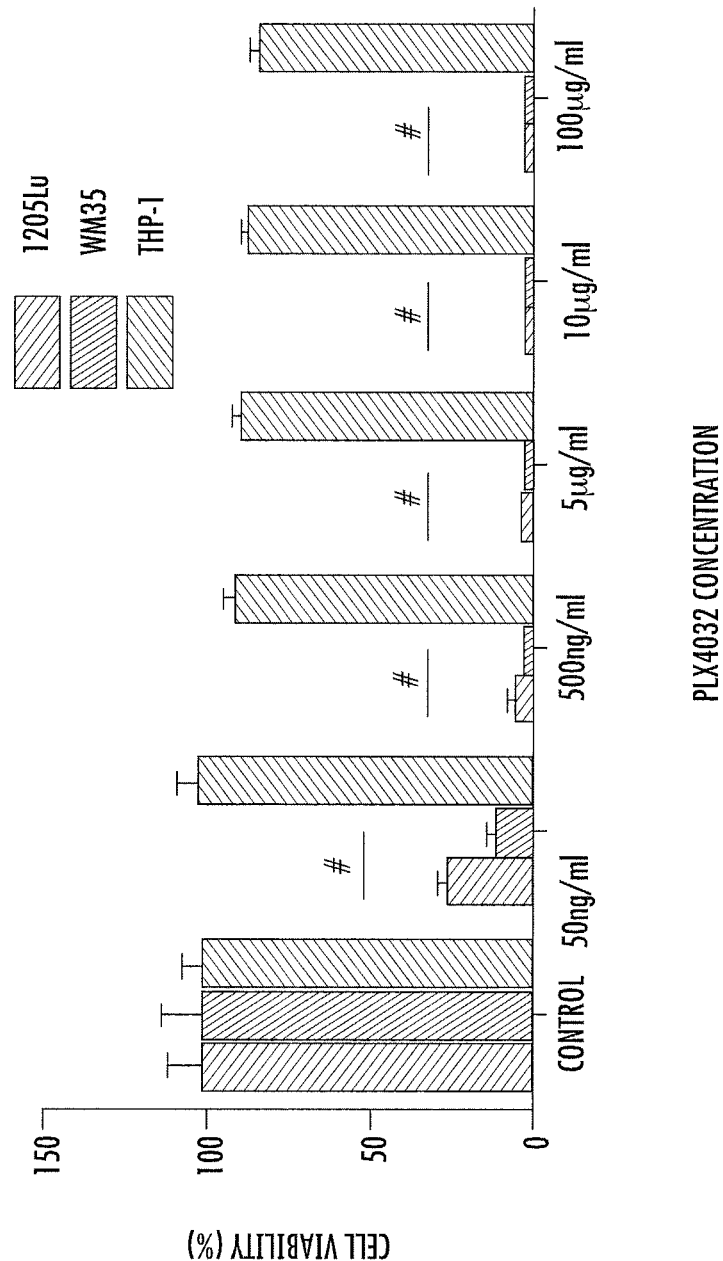
FIG. 7 is a graph depicting cell viability at different free PLX4032 concentrations.
Figure 8:
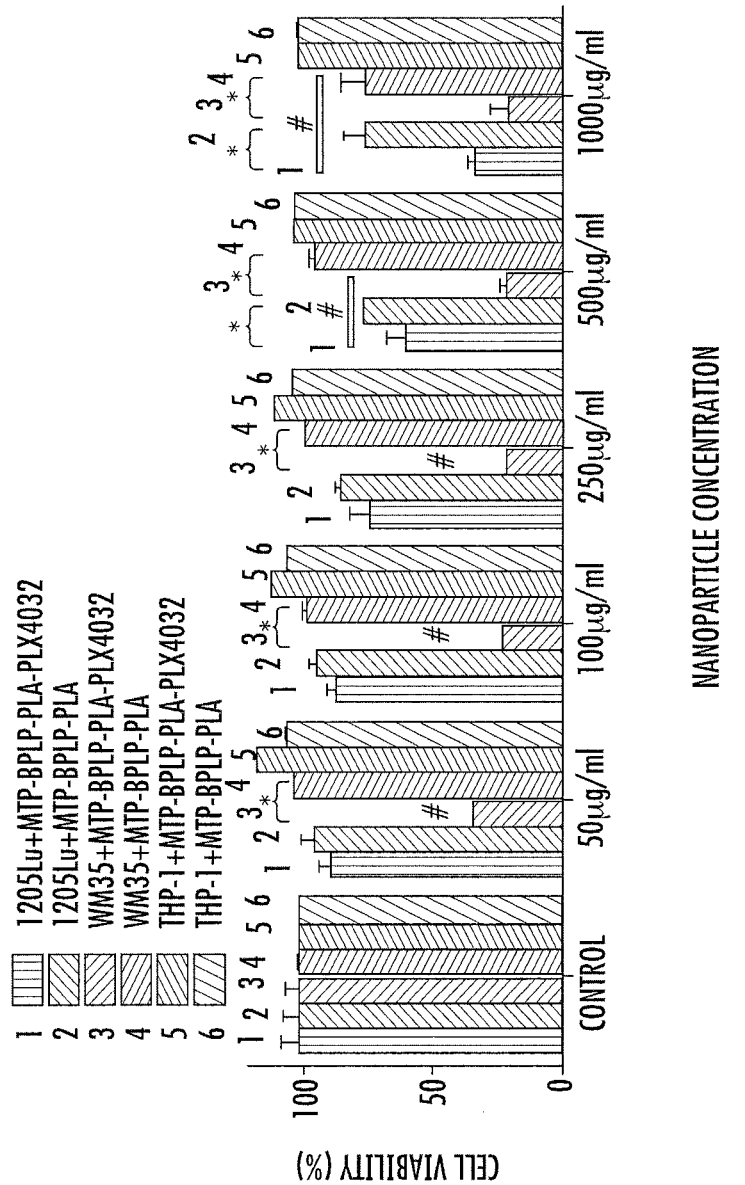
FIG. 8 is a graph depicting cell viability for different concentrations of nanoparticles described herein.
Figure 9:
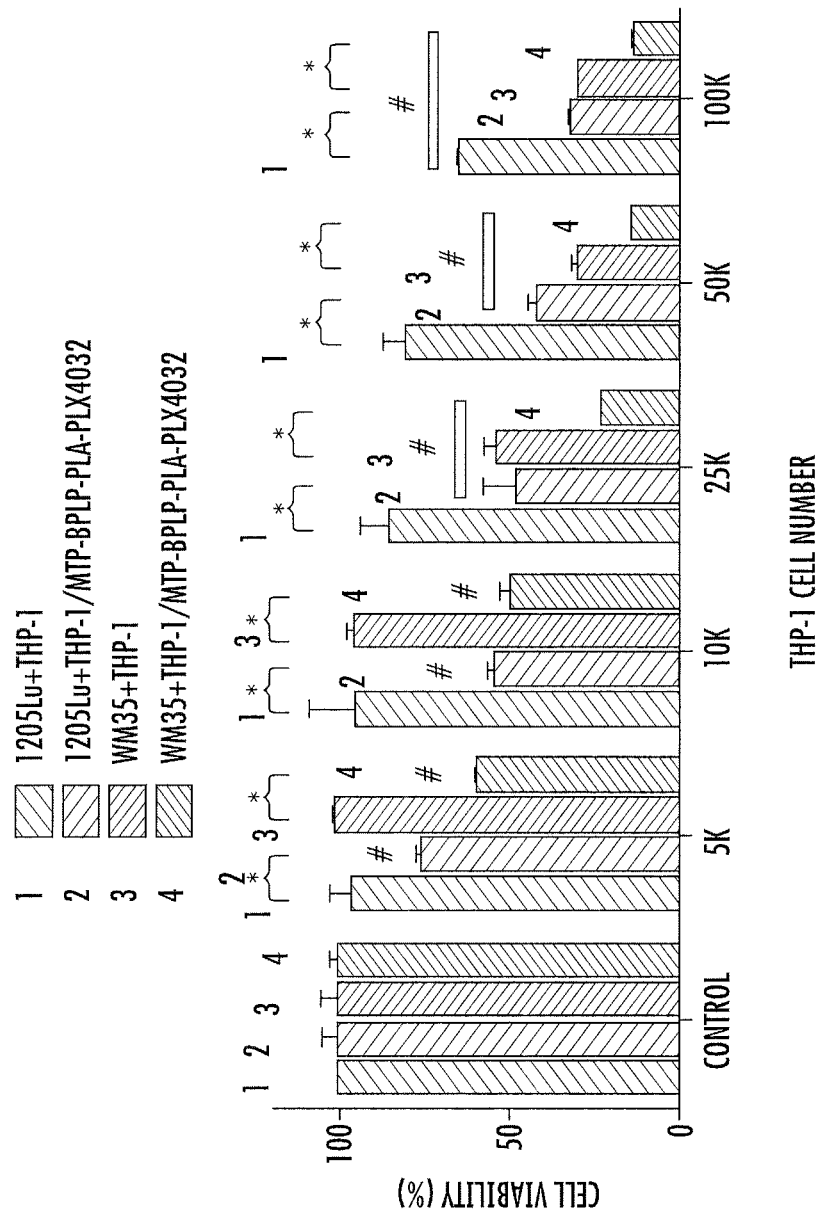
FIG. 9 is a graph depicting cell viability for different nanoparticle-bearing THP-1 cell numbers.
Figure 15:
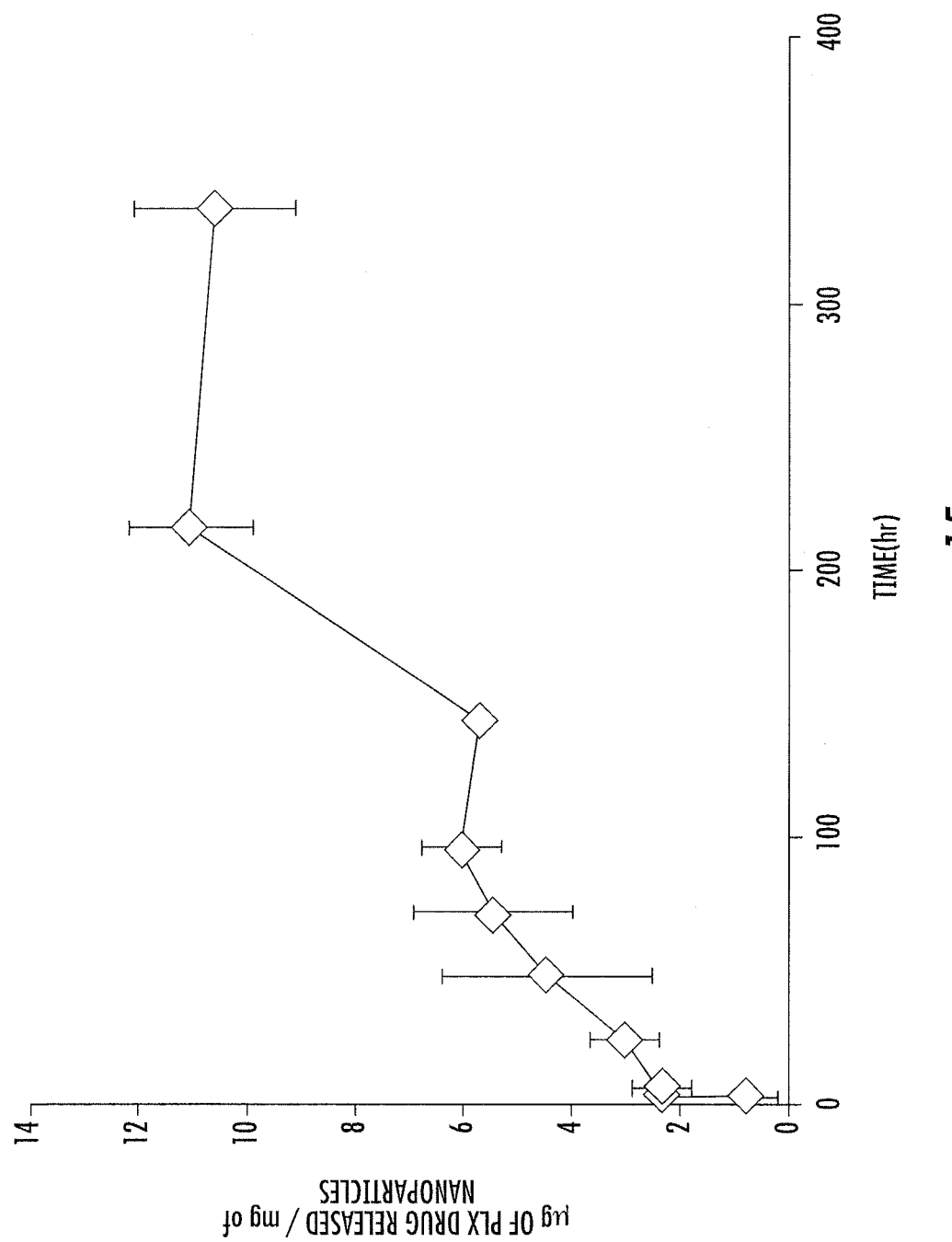
FIG. 15 is a release profile of PLX4032 drug according to some embodiments disclosed herein.

After examining the binding and nanoparticle delivery capabilities of THP-1 cells to melanoma cells, the next step was to examine the safety and pharmaceutical effects to cancer of this immune cell-mediated nanoparticles delivery system. In order to minimize the potential damage to immune cells and normal tissues, a cancer-specific drug was used. PLX4032 is a chemotherapeutics that particularly inhibits the BRAF V600E oncogene of V600E-positive melanomas [References 40, 41]. Two melanoma cell lines investigated here, 1205Lu (high metastasis) and WM35 (low metastasis), are both BRAF mutant with V600E expression [References 26, 41]. First, we found that free PLX4032 itself selectively killed 1205Lu and WM35 at concentrations at 50 ng/ml (FIG. 7). FIG. 7 shows free PLX4032 toxicity to THP-1, WM35 and 1205Lu cells after 24 hrs incubation. With a PLX4032 concentration higher than 5 g/ml, almost 100% kill of melanomas was achieved. However, no significant viability reduction of THP-1 cells was observed even at higher concentrations of 100 μg/ml. Second, in vitro drug release studies showed sustained release of PLX4032 from our nanoparticles (FIG. 15). FIG. 15 is an in vitro PLX4032 drug release profile in PBS at 37° C. No clear burst release was observed in the release curve, which is believed to be important to minimize the side effects and achieve high therapeutic outcomes. The drug release rates in embodiments described herein can be controlled by varying the BPLP:lactide ratio of BPLP-PLA25. Third, we tested the effects of drug-free MTP-BPLP-PLA nanoparticles and PLX4032 loaded MTP-BPLP-PLA nanoparticles on THP-1 cells and melanoma cells. As shown in FIG. 8, which illustrates cytotoxicity of MTP-BPLP-PLA and MTP-BPLP-PLA-PLX4032 nanoparticles to THP-1, WM35 and 1205Lu cells after 7 days incubation, pristine BPLP-PLA nanoparticles without drugs did not significantly reduce the THP-1 cell viability at concentrations as high as 1000 μg/ml. For 1205Lu and WM35 melanomas, pristine MTP-BPLP-PLA nanoparticles without drugs exhibited toxicity at 1000 μg/ml. After 7 days incubation, PLX4032 loaded nanoparticles killed more melanomas than pristine MTP-BPLP-PLA nanoparticles without drugs, especially for WM35, which indicated a significant difference at 50 μg/ml of nanoparticles. The cell viability of both 1205Lu and WM35 melanoma cells significantly reduced to around 30% at 1000 g/ml after 7 days incubation with MTP-BPLP-PLA-PLX4032 suggesting the drug released from nanoparticles was effective to kill melanomas. Most importantly, we used PLX4032 loaded nanoparticle to treat THP-1 cells first. After removal of free nanoparticles, THP-1 cells were co-cultured with 1205Lu/WM35 cells (2 k/well) with different THP-1 to melanoma ratios for 7 days culture. THP-1 cells without any nanoparticles were served as controls. Compared with pristine THP-1, i.e., THP-1 without nanoparticles, nanoparticle-bearing THP-1 significantly decreased the viability of both 1205Lu and WM35 even at the lowest THP-1 amount used of 5 k per well, as demonstrated in FIG. 9. FIG. 9 shows THP-1 mediated nanoparticles delivery and drug release effects on melanoma cells with different THP-1 number (per well) to melanoma cell number (2 k/well) after 7 days incubation. With increasing amount of THP-1 cells added, melanoma cell were killed more, probably due to activated macrophages' ability to release tumor necrosis factor that can kill cancer cells [Reference 42]. Again, THP-1 cells that engulfed PLX loaded nanoparticles further reduced both 1205Lu and WM35's viability than pristine THP-1 at higher ratios. Since we have noticed nanoparticles can be transported from THP-1 to melanomas, PLX4032 were sequentially released and effectively treated melanomas. Noticeably, THP-1 mediated drug delivery was more effective for WM35 than that for 1205Lu. Thus, our immune cell-mediated nanoparticle delivery strategy is valid to transport therapeutics to melanoma cells.

Methods.

Materials.

Chemicals for BPLP-PLA synthesis were purchased from Sigma-Aldrich. THP-1 cells were purchased from ATCC. Human melanoma cells, WM35, 1205Lu, and GFP-tagged 1205Lu melanoma cells were purchased from the Wistar Institute. RPMI-1640 medium, Leibovitz's L-15 medium, 2-mercaptoethanol, Alexa Fluor® 647 Goat Anti-Rat IgG (H+L), and cell dissociation solutions were all obtained from Life Technologies. Fetal Bovine Serum (FBS) was obtained from Atlanta Biologicals. Phorbol 12-myristate 13-acetate (PMA), MCDB 153 medium, lipopolysaccharide (LPS) from *Escherichia coli* and Dulbecco's phosphate-buffered saline (DPBS), and other chemicals were all purchased from Sigma-Aldrich. CCK-8 assay kit was obtained from Dojindo. PLX4032 drug was purchased from Chemie-Tech. Muramyl tripeptide (MTP) was obtained from InvivoGen. Integrin αM antibody (M1/70) (CD1 b) was purchased from Santa Cruz Biotechnology.

Cell Culture.

THP-1 and WM35 were maintained with RPMI-1640 medium with 10% FBS and 0.05 mM 2-mercaptoethanol at 37° C. under 5% $CO_2$. Before THP-1 uptake, cell binding and pharmacological studies, THP-1 cells were first differentiated by 200 nM PMA in RPMI-1640 medium for 3 days followed by 1 day in PMA-free medium. Then, 1 μg/ml LPS was applied to stimulate differentiated THP-1 for 24 h. 1205Lu and GFP-tag 1205Lu were cultured in a tumor medium containing a 4:1 mixture of MCDB 153 medium with 1.18 g/L sodium bicarbonate and Leibovitz's L-15 medium with 2 mM L-glutamine. The mixed medium were supplemented with 0.005 mg/ml bovine insulin, 1.68 mM $CaCl_2$, and 2% fetal bovine serum and 1205Lu cells were cultured at 37° C. under 5% $CO_2$.

Polymer Synthesis and Nanoparticle Fabrication.

BPLP was synthesized by a polycondensation of reacting citric acid, 1,8-octanediol, and L-serine at 140° C. [Reference 28]. Next, BPLP-PLA was synthesized via a ring-opening polymerization [Reference 25]. The feeding molar ratio of BPLP to L-lactide monomers was 1:50. The characterization of BPLP-PLA can be found in our previous reports [Reference 25]. BPLP-PLA nanoparticles were prepared by a single emulsion method. Briefly, 50 mg BPLP-PLA polymer was dissolved in 2 ml chloroform solution, which was added drop-wise into 20 ml 5 wt % poly(vinyl alcohol) (87% hydrolyzed, Mw of 87 k Da) solution during sonication. The solution was stirred vigorously overnight for solvent evaporation. Resulting nanoparticles were centrifuged and washed by deionized (DI) water three times before being lyophilized. PLX4032 drug loaded nanoparticles (BPLP-PLA-PLX4032) were prepared by dissolving 10 wt % (to BPLP-PLA) of PLX4032 in 200 μL DMSO and mixing with the polymer solution, followed by the same single emulsion and washing procedure to obtain drug loaded nanoparticles. MTP was conjugated to nanoparticles by carbodiimide chemistry, according to an established protocol [Reference 43]. Specifically, 40 mg nanoparticles were dispersed in 20 ml MES buffer (pH 4.5) by sonication. 20 mg 1-ethyl-3-(3-dimethylaminopropyl) carbodiimide (EDC) and 20 mg N-hydroxysuccinimide (NHS) were added sequentially to activate the carboxyl groups of BPLP-PLA nanoparticles under stirring for 1 hr each at room temperature. Then, 100 g MTP was then added into the mixture and stirred for 4 hrs. MTP conjugated nanoparticles were washed by DI water for three times before lyophilized as well.

Nanoparticle Characterizations.

Figure 11:
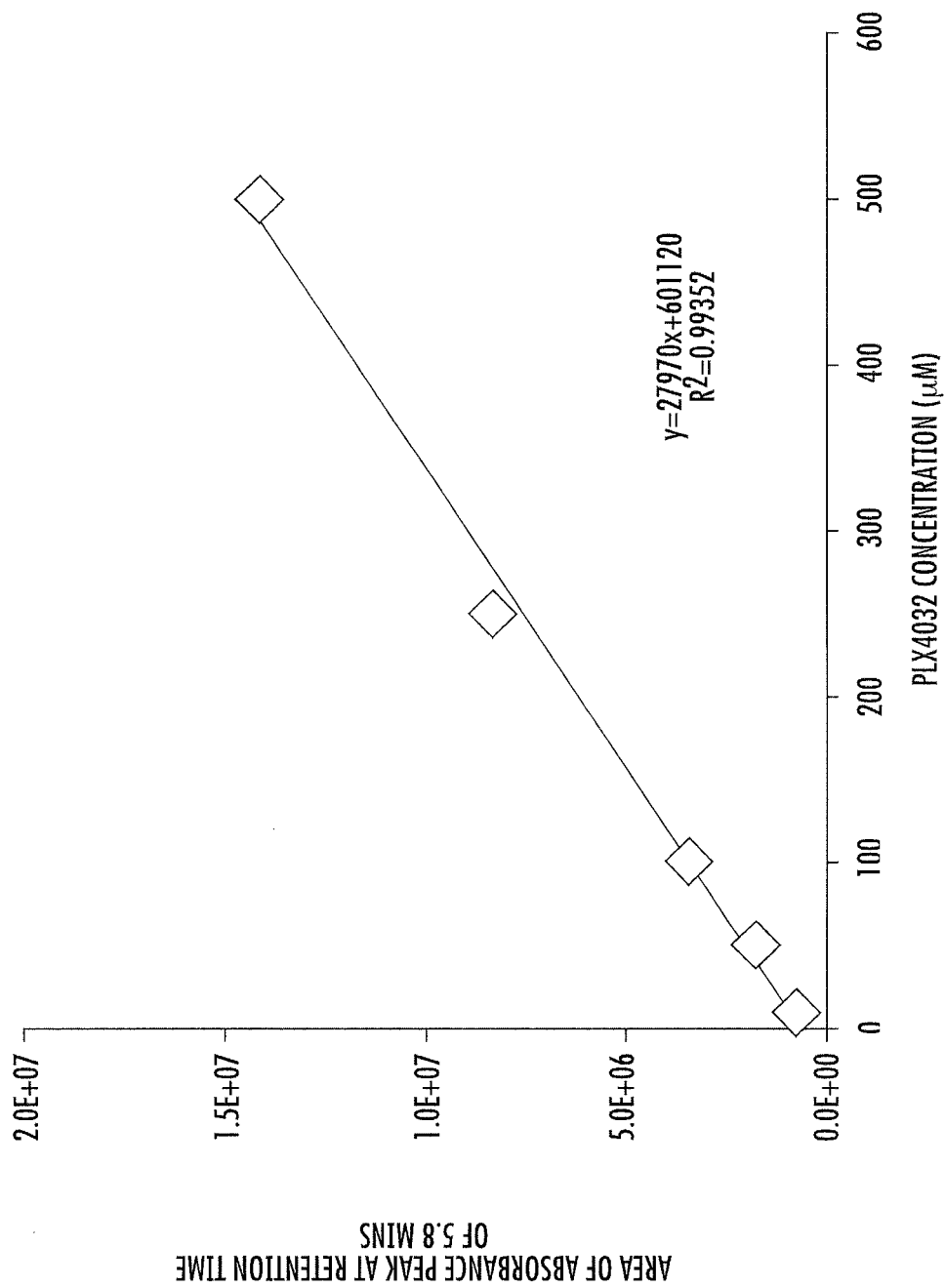
FIG. 11 is a calibration curve of PLX4032.

The particle size, size distribution and zeta potential of various nanoparticles were measured by dynamic light scattering (DLS, Malvern Zetasizer ZS). The chemical structures and morphology of nanoparticles were characterized by Fourier transform infrared spectroscopy (FTIR, Bruker Vertex V70) and scanning electron microscopy (SEM, FEI Nova NanoSEM 630). For fluorescence spectra were measured by a fluorescence spectroscopy (Horiba FMax-4) with a slit size of 2 nm by 2 nm. The concentration of nanoparticles was 20 μg/ml in DPBS. The drug loading efficiency was measured by using a high performance liquid chromatography (Shimadzu) equipped with a photodiode array detector (Shimadzu) and a Phenomenex Kinetex C18 column. The mobile phase was a mixture of 40% acetonitrile and 60% DI water, and the flow rate was 1 ml/min. PLX4032 concentration was determined by reading the absorbance at 270 nm, and a calibration curve was built on same conditions (FIG. 11). For drug release tests, 50 mg PLX4032 loaded nanoparticles were dispersed in 1 ml 50 mM PBS and placed in a dialysis bag with MWCO of 1000 Da. The dialysis bag was kept in 5 ml PBS in a tube and shaken at 37° C. At each time points, 0.5 ml release solution was taken out for HPLC measurement and a fresh 0.5 ml PBS was added into the tube.

THP-1 Uptake.

Differentiated THP-1 cells were lifted by cell dissociation buffer and used for further studies. THP-1 uptake studies were carried out by incubating $1 \times 10^6$ differentiated THP-1 cells and 200 g/ml BPLP-PLA and MTP-BPLP-PLA nanoparticles in 1 ml DPBS at 37° C. for 2 hrs on a rocker, respectively. Afterwards, THP-1 cells were washed gently by DPBS three times, and then subjected for characterizations and further studies.

Immunofluorescence Staining.

To prevent non-specific binding, THP-1 cells were blocked by 1% BSA for 1 hr at room temperature and incubated with 2 μg/ml CD11b rat anti-mouse mAb overnight at 4° C. Cells were then stained with Alexa Fluor® 647 Goat anti-rat IgG (H+L) (2 μg/ml) for 1 hr at room temperature. THP-1 cells incubated with secondary antibodies were served as controls. The cells were fixed by 4% paraformaldehyde at room temperature for 30 mins and subjected to flow cytometry and confocal microscopy. For confocal microscopy, DAPI was used to stain the nucleus of THP-1 cells.

Cell Binding Studies Under Static Conditions.

Two melanoma cell lines, 1205Lu (high metastasis) and WM35 (low metastasis) were selected as BRAF mutant melanomas. Nanoparticle loaded THP-1 cells were incubated with GFP-tagged 1205Lu in 1 ml DPBS with 1 million cells each at 37° C. for 2 hrs on a rocker. The resulting cells were gently washed with DPBS for three times and fixed with 4% paraformaldehyde at room temperature for 30 mins. Cell binding was analyzed by using a BD Fortessa LSRII flow cytometry and FACS analysis were performed by using FlowJo 10. Confocal microscopy was performed in inverted mode on an Olympus Fluorview 100 confocal microscope. For both flow cytometry and microscopy, FITC channel was set to detect the fluorescence from GPF-tagged 1205Lu and Texas Red channel was used to detect the fluorescence from BPLP-PLA nanoparticles. For WM35 binding studies, cells were stained by CellTrace™ CFSE (Life Technologies) first to obtain green fluorescence.

Cell Binding Studies Under Shear Flow Conditions.

To simulate the shear flow conditions of the blood flow, cell binding studies were performed in a uniform shear flow by using a cone plate viscometer (Thermo). 1 million nanoparticles loaded THP-1 cells were mixed with GFP-tagged 1205Lu at 1:1 ratio in 1 ml DPBS. The cell mixtures were immediately added into the cone-plate viscometer and exposed to shear flows at shear rates varied from $50\ s^{-1}$ to $200\ s^{-1}$ at room temperature for 1 hr. Then, the cells were removed from the cone-plate viscometer and washed twice by DPBS. The cells were fixed by 4% paraformaldehyde at room temperature for 30 mins and subjected for confocal and flow cytometry studies as described in above section.

Pharmacological Studies.

First, free PLX4032 toxicity and selectivity were confirmed by adding PLX4032 solutions at different concentrations into 96 well plates with THP-1, 1205Lu and WM35 cells separately (cell seeding density=5,000 cells/well). After 24 hrs incubation, the cells were washed with PBS twice and supplemented with 10 μl CCK-8 in 100 μl RPMI-1640 medium in each well. After 2 hrs incubation, the absorbance at 450 nm of each well was measured by a micro-plate reader (TECAN, infinite M200 PRO) and converted to the cell viability by normalized to control (tissue culture plates). Next, MTP-BPLP-PLA nanoparticles with and without PLX4032 loaded were dispersed in RPMI-1640 medium in various concentrations, followed by incubation with THP-1, 1205lu and WM35 cells (2,000 cells/well) separately in same conditions for 7 days. At last, MTP-BPLP-PLA-PLX4032 loaded THP-1 cells and pristine THP-1 cells were seeded with 1205lu or WM35 cells (2,000 cells/well) together with different ratios for 7 days, respectively. The cell viabilities were tested by CCK-8 assays as well.

Statistical Analysis.

All data was recorded as mean±standard error unless otherwise stated. All statistical analyses were performed via one-way ANOVA on GraphPad Prism 6.0. For all studies, n equals 6, unless specifically stated otherwise.

EXAMPLE 2

Tissue Engineering

A circulating cell mediated delivery platform for tissue engineering can be delineated and implemented through the following approaches.

Figure 16:
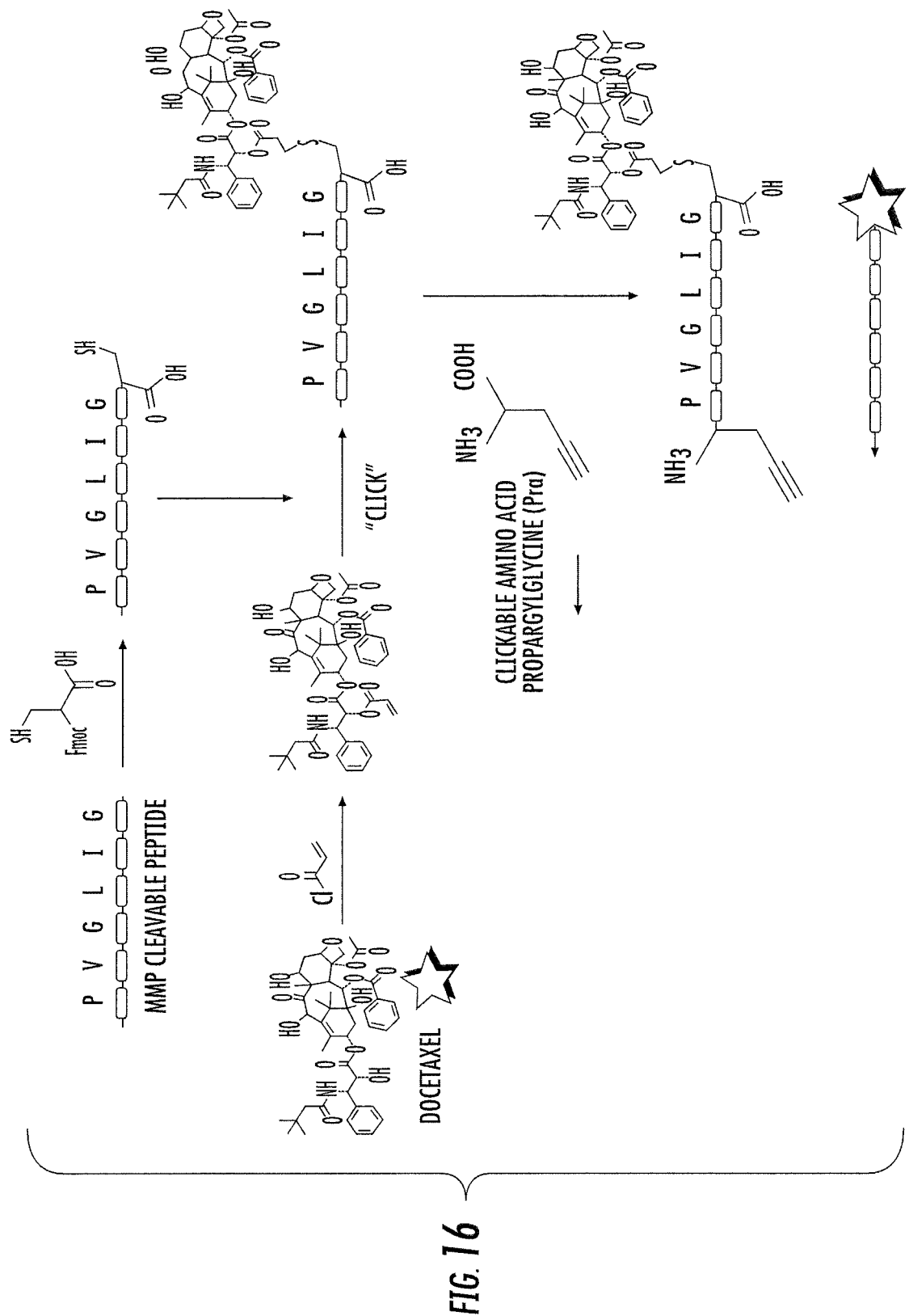
FIG. 16 is a schematic showing synthesis of a nanoparticle according to some embodiments described herein.
Figure 17B:
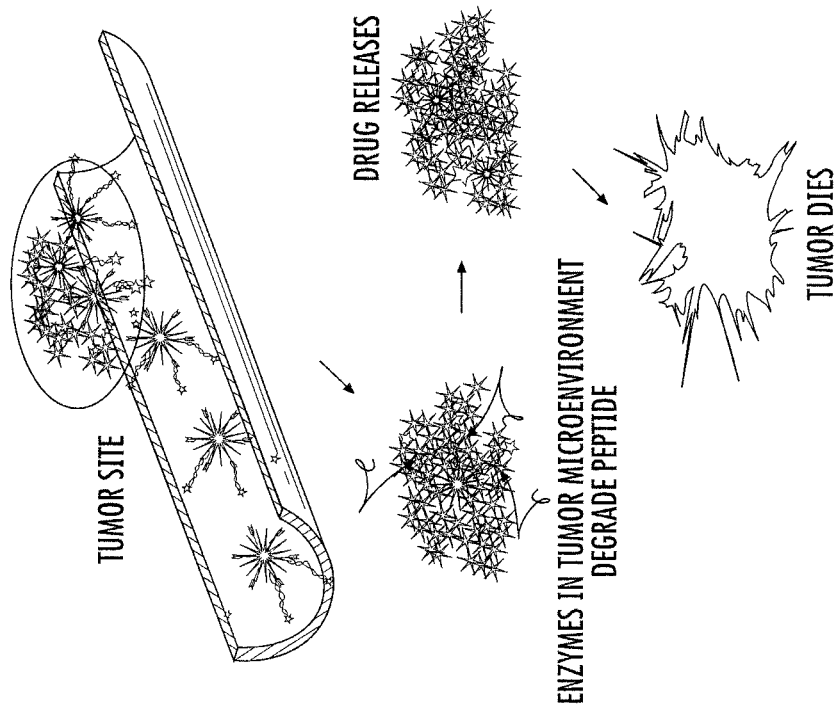
FIGS. 17A and 17B are schematics showing nanoparticles, cell-nanoparticle conjugates, and use of the same according to some embodiments described herein.
Figure 17A:
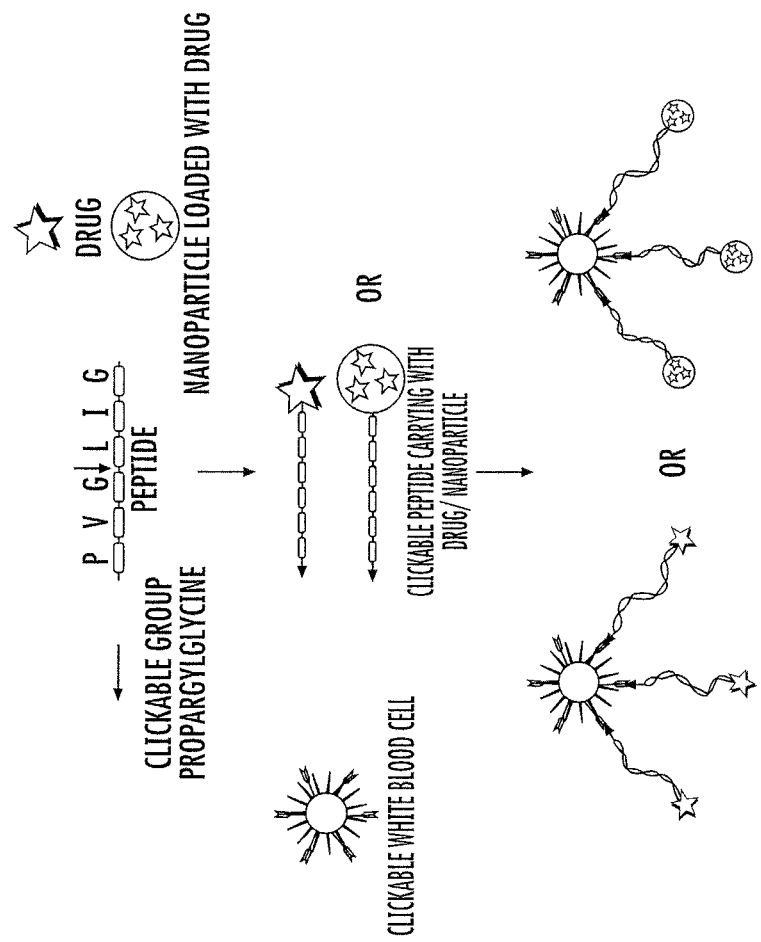

Approach 1:

Synthesis and characterization of clickable enzyme-sensitive degradable peptide and its conjugation to cancer drugs or drug-loaded nanoparticles. Matrix metalloproteinase (MMPs)-sensitive peptide, PVGLIG, was chosen as a model enzyme-sensitive peptide since diseased/injured/inflamed (DII) tissues including cancer tissues always present elevated levels (concentrations) of MMPs [References 44, 45]. Docetaxel was chosen as a model cancer drug. Through click chemistry, we obtain an enzyme (MMP-2)-sensitive peptide with one end capped with docetaxel or nanoparticles (loaded with docetaxel) and another end carrying a clickable alkyne group for future click bioconjugation with live cells, drugs, or nanoparticles, as shown in FIGS. 16 and 17A. The nanoparticle or drug-modified clickable peptides, may be referred to as "NP-PT-alkyne" or "Drug-PT-alkyne." Here "NP" refers to a nanoparticle, "Drug" refers to a drug-loaded nanoparticle, and "PT-Alkyne" refers to an enzyme-sensitive degradable peptide with a clickable group where the clickable group is an alkyne.

Figure 19:
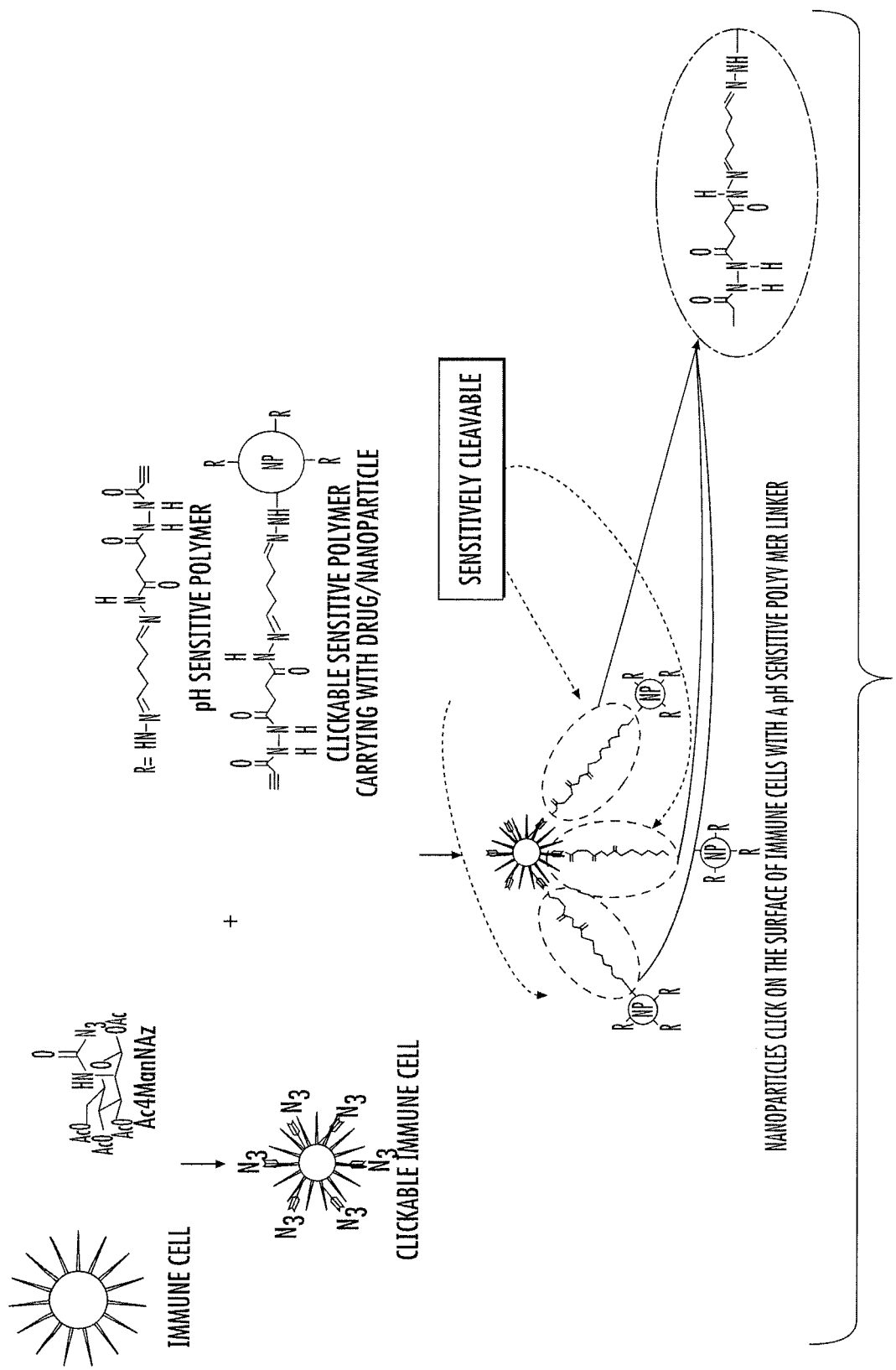
FIG. 19 is a schematic showing formation of a cell-nanoparticle conjugate according to some embodiments described herein.

Approach 2:

Synthesis and characterization of a clickable pH-sensitive degradable polymer and its conjugation to drugs, e.g., cancer drugs, or drug-loaded nanoparticles. A hydrazone group, with a structure $R_1R_2C=NNH_2$, is chosen as the pH sensitive group to be incorporated into the clickable pH-sensitive degradable polymer. FIG. 19 depicts a clickable pH sensitive degradable polymer comprising a hydrazone group. Hydrazone-based bonds are stable at or near a neutral or slightly basic pH, e.g., in the blood, having a pH of about 7.4, but can be broken, e.g., by hydrolysis, in an acidic environment, e.g., in a tumor extracellular environment that has a pH of about 6.5-6.9. A pH-sensitive degradable polymer with a drug or drug-loaded nanoparticle on one end and a clickable group for further conjugation with live cells, drugs, nanoparticle, etc., e.g., an alkyne group, on the other end is obtained. (See FIG. 19) The drug-loaded nanoparticle-modified or drug-modified clickable pH sensitive degradable polymers may be referred to as "NP—PH-alkyne" or "Drug-PH-Alkyne." Here, "NP" refers to a nanoparticle, "Drug" refers to a drug-loaded nanoparticle, and "PH-Alkyne" refers to a pH sensitive polymer with a clickable group where the clickable group is an alkyne.
Protocol.

Figure 20:
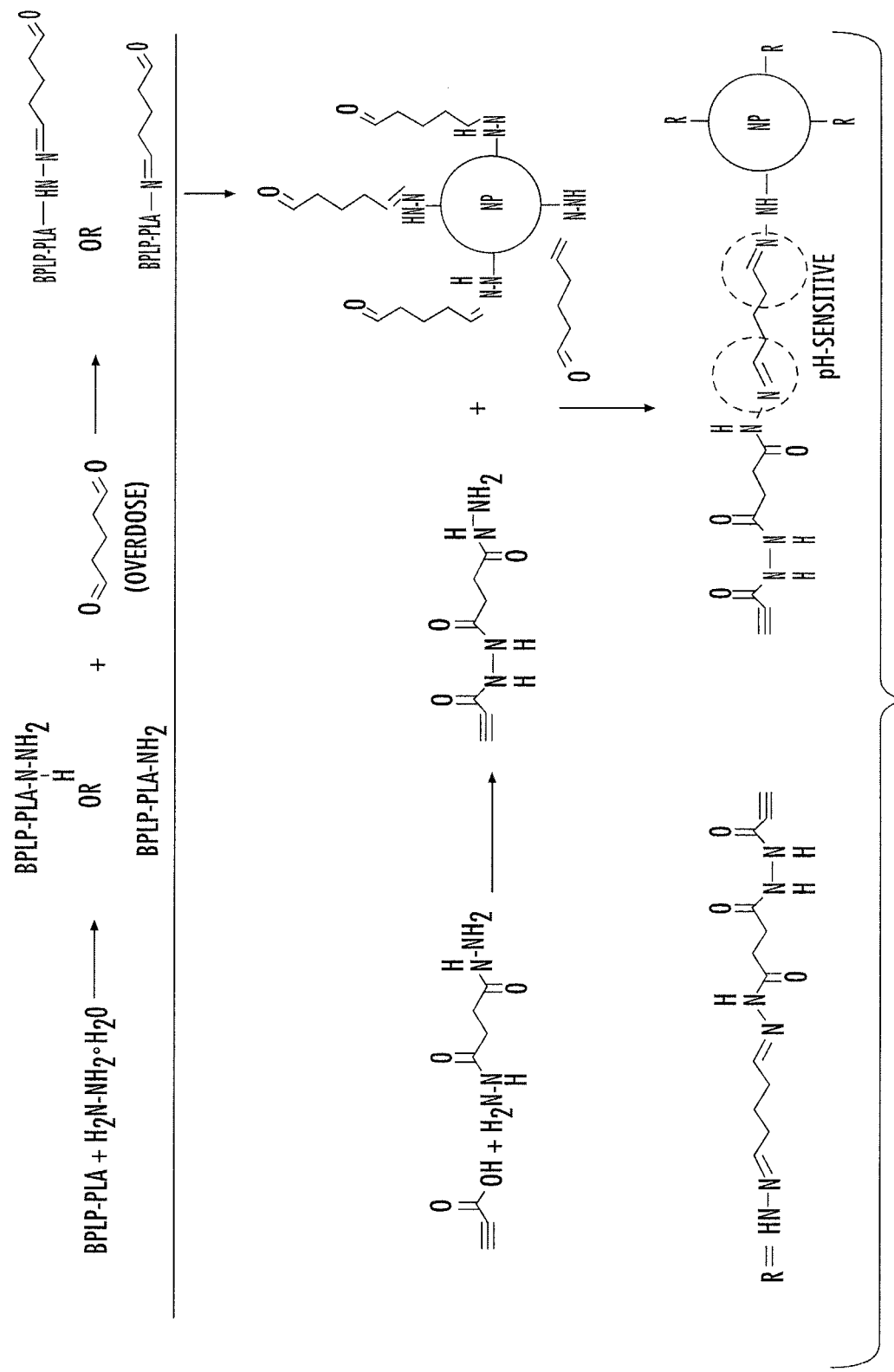
FIG. 20 is a schematic showing formation of a nanoparticle according to some embodiments described herein.

A clickable pH-sensitive degradable polymer conjugated to cancer drugs or cancer drug-loaded nanoparticles, e.g., NP—PH-alkyne or Drug-PH-Alkyne, may be formed by the protocol illustrated in FIG. 20.

Formation of Clickable Succinic Dihydrazide:

0.5 g propiolic acid and 0.77 g EDC (0.95 g EDC.HCl) were dissolved in 20 ml MES and stirred for one hour. Next, 0.57 g NHS was added, and the mixture was stirred for one hour. Then, 0.8 g succinic dihydrazide was added, and the resulting mixture was stirred for 48 hours. The product was freeze-dried and kept at −20° C.

Formation of BPLP-PLA-CHO:

10 g of BPLP was dissolved in 50 mL of chloroform, and then 10 mL of hydrazine hydrate was injected therein, and the resulting mixture was stirred for 3 hours. Then, 200 mL of a 1:1 mixture of ethanol and $H_2O$ was added. The resulting mixture was rotary evaporated to completely dry and remove unreacted hydrazine hydrate. The dried product was then dissolved in 20 mL of ethanol and injected in 3 mL triethylamine and 20 mL of 50% glutaraldehyde and stirred for 24 hours. The resulting product was concentrated using rotary evaporation, precipitated in DI water, freeze dried, and stored in a refrigerator.

Formation of pH Sensitive Nanoparticles:

Dissolve 50 mg of BPLP-PLA-CHO in chloroform, dissolve 50 mg of succinic dihydrazide in 10 mL of 5 wt % PVA solution, and use standard nanoparticle preparation process with ultrasonic.

Figure 21:
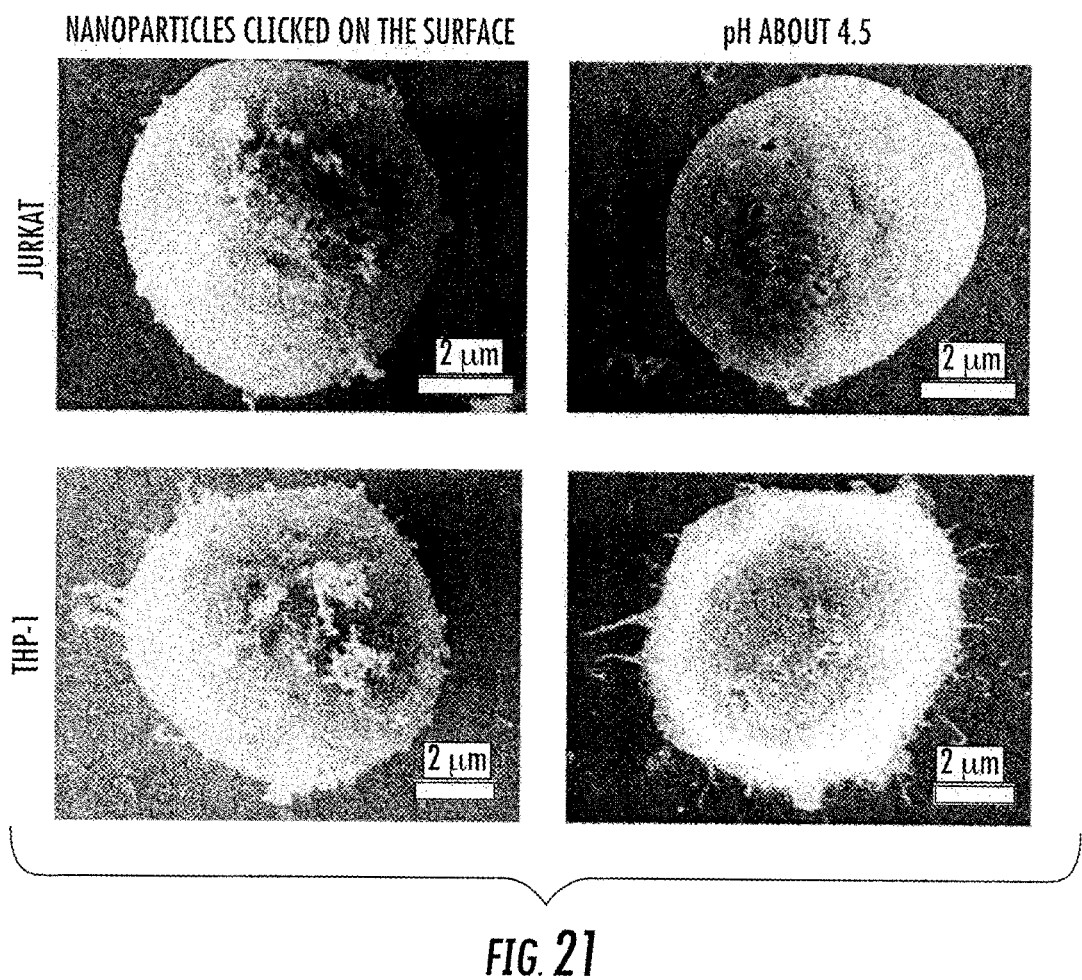
FIG. 21 depicts the surface of the cell of cell-nanoparticle conjugates according to some embodiments described herein at different pH values.
Figure 22:
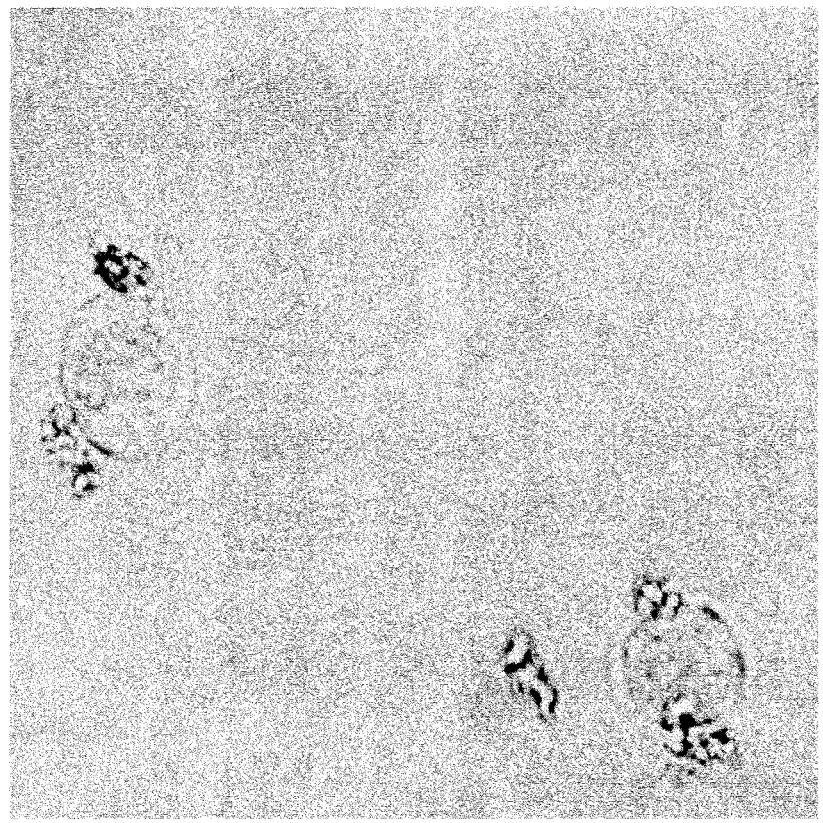
FIG. 22 depicts cell-nanoparticle conjugates according to some embodiments described herein.

Approach 3:

Further conjugation of NP-PT-alkyne, Drug-PT-Alkyne, NP—PH-alkyne, or Drug-PH-Alkyne to cells, e.g., autologous immune cells, is disclosed. These are exemplary nanoparticle-cell conjugates as described herein. As shown in FIGS. 17A and 19, and not intending to be bound by theory, first, immune cells such as neutrophil, which is a type of white blood cell, will be isolated from human blood and then will undergo metabolic incorporation of azido sugars in the cell surface with peracetylated N-azidoacetylmannosamine (Ac4ManNAz) to synthesize azide (N3)-presenting immune cells (denoted as "IC—N3" for "Immunce Cell-Azide"). It has been shown that the azide modification does not compromise macrophage viability and functions [Reference 15]. Second, the IC—N3 will then click with NP-PT-alkyne, Drug-PT-alkyne, NP—PH-alkyne, or Drug-PH-alkyne to synthesize immune cell-peptide-nanoparticlesor immune cellpeptide-drug (e.g., denoted as "IC-PT-NPs or IC-PT-Drug") conjugates. Here "IC" is derived from IC—N3 and "PT-Drug" and "PT-NP" are derived from PT-Drug-Alkyne and PT-NP-Alkyne, respectively. For example, IC-PT-NP is derived from clicking IC—N3 and PT-NP-alkyne together. Third, these immune cell drug or immune cell-drug-loaded nanoparticle conjugates, e.g., IC-PT-NPs or IC-PT-Drugs, can be injected into a blood vessel, travel through circulation, and specifically target and bind to DII tissue such as tumors. For example, PT will be degraded to release drugs or drug-encapsulated NPs in response to the high concentration of MMPs in DII tissues or tumors. (See FIG. 17B.) In other embodiments, bonds of PH will be broken when exposed to an acidic environment e.g., a tumor extracellular environment that has a pH of about 6.5-6.9. FIG. 21 and FIG. 22 show NP—PH clicked to the surface of (not inside of or swallowed by) THP-1 and Jurkat cells at neutral pH, and these NP—PHs are noticeably dissociated from the surface of these cells at pH 4.5, as shown in FIG. 21.

Figure 18:
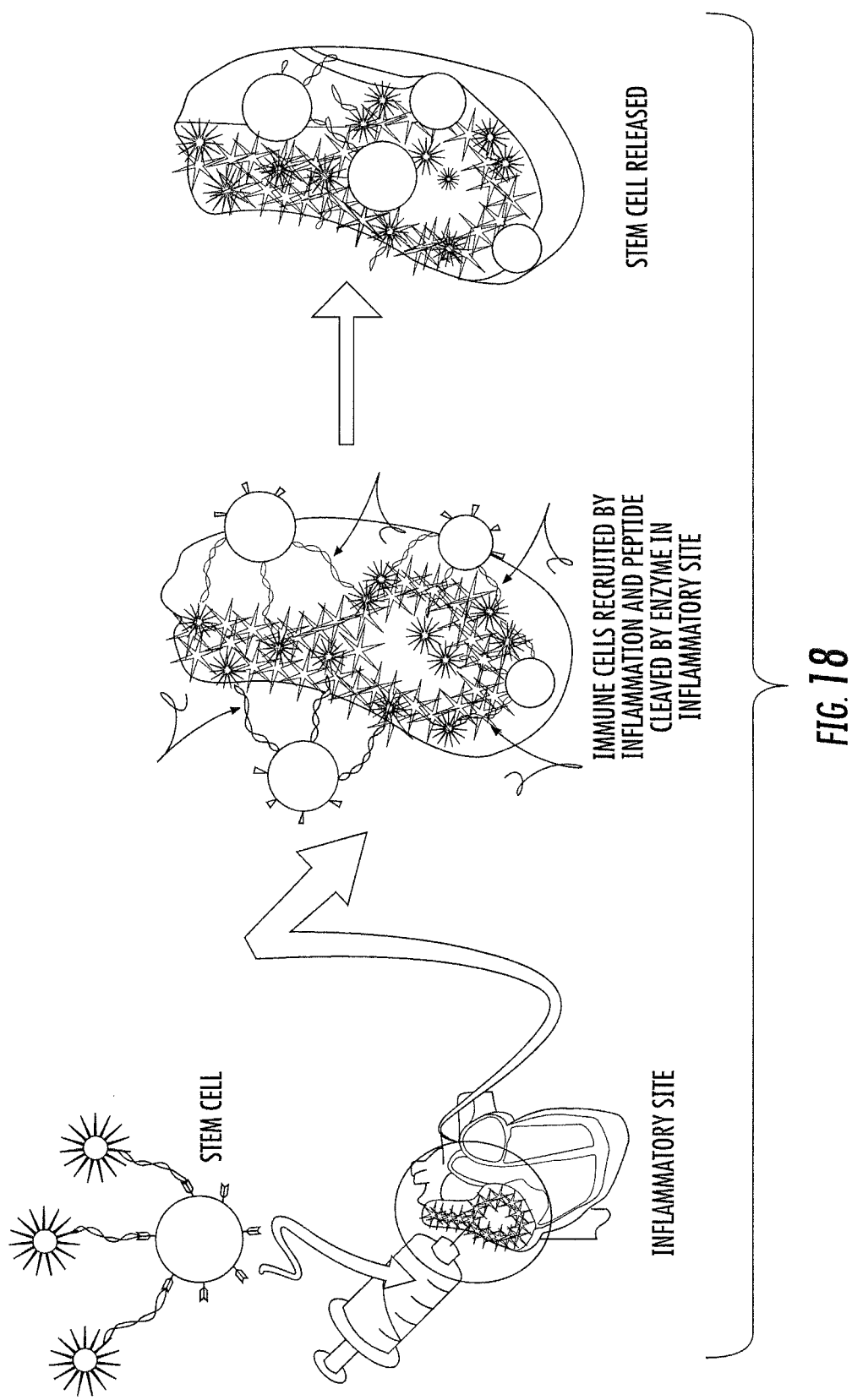
FIG. 18 is a schematic showing use of cell-nanoparticle conjugates according to some embodiments described herein at an inflammatory site.

Approach 4:

Immune cell-mediated stem cell delivery for tissue engineering, exemplified for ischemic cardiac tissue regeneration. In this approach (see FIG. 18), Stem cells and immune cells are clicked together via peptides, e.g., the MMP-sensitive peptides. Stem cell-N3, like IC—N3, will be synthesized and then clicked with IC—N3 through alkyne-peptide-alkyne to form cell assemblies, stem cells-PT-immune cells (SCs-PT-ICs). SCs-PT-ICs will be injected into ischemic heart muscles. Not intending to be bound by theory, ICs will bind and reside in inflamed cardiac tissues to significant improve stem cell retention and improve local immune cell populations thus immune responses to promote vascularization and wound healing. PT will be degraded over time thus fully releasing SCs for tissue regeneration.

Figure 23:
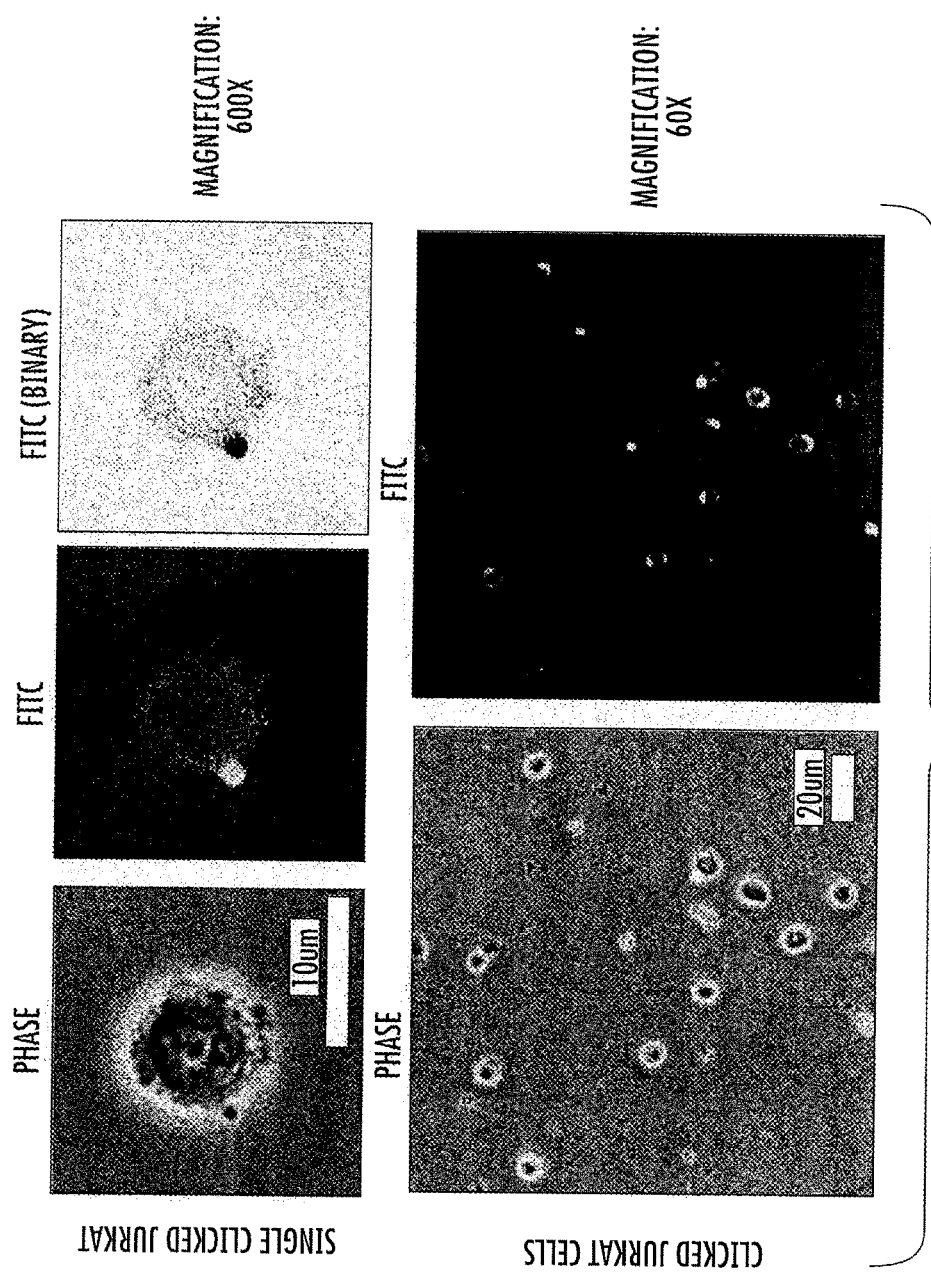
FIG. 23 shows the confocal images of cell-nanoparticle conjugates according to some embodiments described herein.

Approach 5:

IC-PT-NPs, IC-PT-Drugs, IC—PH—NPs, IC—PH-Drugs, and other cell-nanoparticle conjugates described herein, particularly where the cell is an immune cell, may be used in the treatment of brain cancer. (See FIGS. 23, 24 and 25) Immune cells have the innate property of forming gaps on the blood brain barrier (BBB) and migrating through the BBB to approach a brain tumor in the brain. Transendothelial migration of immune cells is a multi-step process. Immune cells first respond to a biochemical signal coming from chemokines released from the brain as a result of some type of inflammation or disease. In responding to the chemokines, immune cells form gaps on the BBB and migrate through the BBB.

Protocol.

Figure 25:
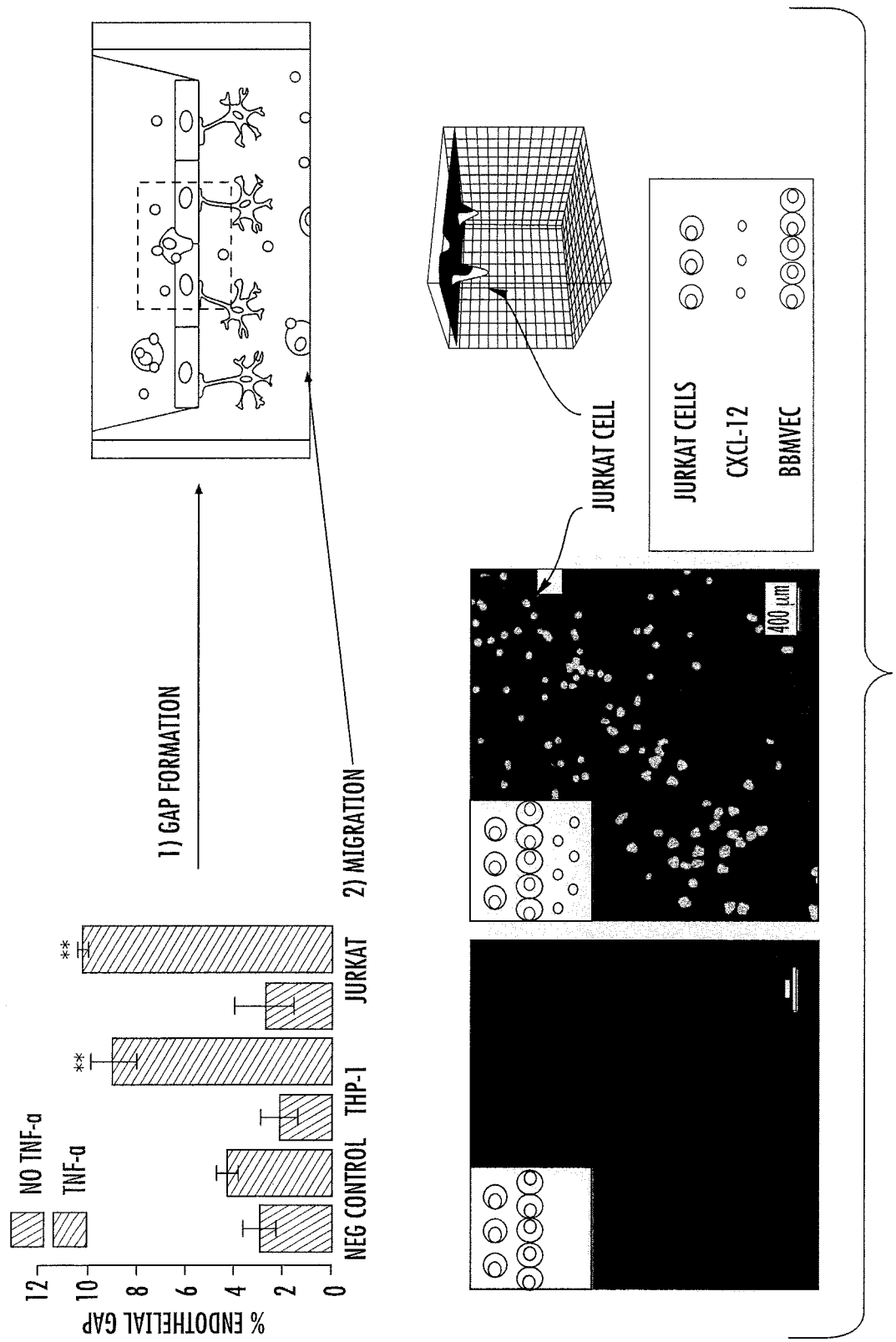
FIG. 25 is a schematic showing use of cell-nanoparticle conjugates according to some embodiments described herein.

In a study as shown in FIG. 25, in a first step, both THP-1 cells (monocytes) and Jurkat cells (lymphocytes) form gaps on brain endothelial cells. This gap formation study was done on a glass coverslip covered with endothelial cells. Once the endothelial cells were exposed to immune cells, the endothelial cells formed gaps. In this study, the endothelial cells were pre-treated with TNF-α to induce inflammation on them so that the endothelial cells will have more protein expression, e.g, of VCAM-1, that is involved in the tethering process of immune cells on endothelial cells.

In a second step, migration happens based on cell-cell interactions between immune cells and endothelial cells. In this study, CXCL-12 was use as a chemoattractant for Jurkat cells. CXCL-12 can be released by diseased astrocytes in the brain.

Results.

Figure 26:
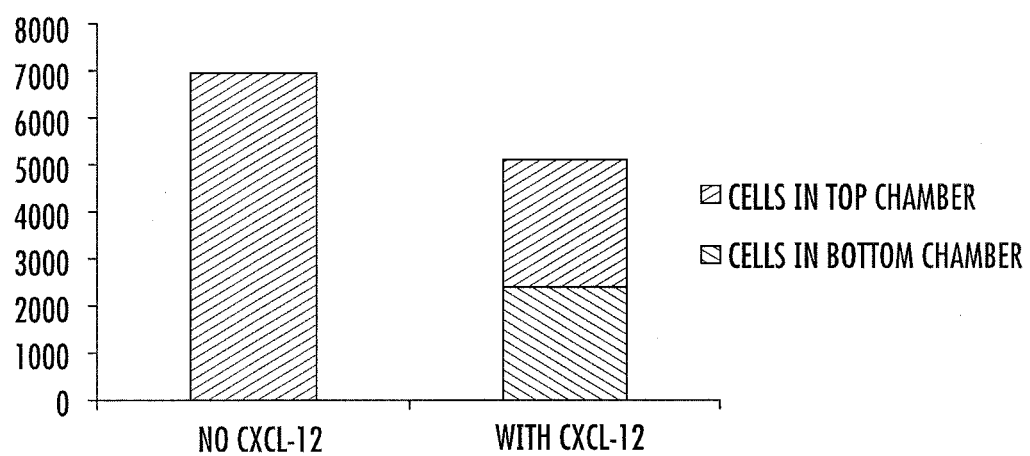
FIG. 26 is a graph depicting the number of cell-nanoparticle conjugates, according to some embodiments described herein, collected from bottom and top chambers with and without the use of CXCL-12.

Clicked Jurkat (immune) cells, e.g., Jurkat cells clicked with BPLP nanoparticles, can migrate through the BBB. Quantitatively, as shown in FIG. 26, clicked Jurkat cells migrated in response to CXCL-12, which is a chemoattractant for Jurkat cells. This shows that clicked immune cells can also be used as a cell vehicle for delivery of nanoparticle drugs to brain cancer.

Some Conclusions from Example 1 and Example 2

Disclosed herein is a newly developed targeted nanomedicine strategy that involves using cells as carriers for targeted delivery of nanoparticles and cells, e.g., stem cells, to targets for the purposes of cancer treatment, tissue regeneration, etc. One examples of this is a "living" delivery of nanoparticles mediated by immune cells, in which macrophages were selected as an example. Biodegradable fluorescent polymeric nanoparticles encapsulated melanoma specific therapeutics, PLX4032, to provide tracking capabilities, safe protection to macrophages, and controlled release of drugs to cancer cells. High uptake of nanoparticles in macrophage was achieved by modifying particles with MTP peptides. The active binding of macrophages to melanomas was confirmed with and without the presence of nanoparticles. Associated with THP-1 cells, nanoparticles were delivered to melanoma cells and consequently released chemotherapeutics to kill cancer cells.

REFERENCES

1. Barreto, J. A.; O'Malley, W.; Kubeil, M.; Graham, B.; Stephan, H.; Spiccia, L. Nanomaterials: Applications in Cancer Imaging and Therapy. Advanced Materials 2011, 23, H18-H40.
2. Yu, M. K.; Park, J.; Jon, S. Targeting strategies for multifunctional nanoparticles in cancer imaging and therapy. Theranostics 2012, 2, 3-44.
3. Kona, S.; Dong, J. F.; Liu, Y.; Tan, J.; Nguyen, K. T. Biodegradable nanoparticles mimicking platelet binding as a targeted and controlled drug delivery system. International journal of pharmaceutics 2012, 423, 516-24.
4. Petros, R. A.; DeSimone, J. M. Strategies in the design of nanoparticles for therapeutic applications. Nat Rev Drug Discov 2010, 9, 615-627.
5. Cole, A. J.; Yang, V. C.; David, A. E. Cancer theranostics: the rise of targeted magnetic nanoparticles. Trends in Biotechnology 2011, 29, 323-332.
6. Kobayashi, H.; Longmire, M. R.; Ogawa, M.; Choyke, P. L. Rational chemical design of the next generation of molecular imaging probes based on physics and biology: mixing modalities, colors and signals. Chemical Society reviews 2011, 40, 4626-48.
7. Sarris, A. H.; Hagemeister, F.; Romaguera, J.; Rodriguez, M. A.; McLaughlin, P.; Tsimberidou, A. M.; Medeiros, L. J.; Samuels, B.; Pate, O.; Oholendt, M.; Kantarjian, H.; Burge, C.; Cabanillas, F. Liposomal vincristine in relapsed non-Hodgkin's lymphomas: early results of an ongoing phase II trial. Annals of oncology: official journal of the European Society for Medical Oncology/ESMO 2000, 11, 69-72.
8. Davis, M. E.; Hsieh, P. C.; Grodzinsky, A. J.; Lee, R. T. Custom design of the cardiac microenvironment with biomaterials. Circ Res 2005, 97, 8-15.
9. Laflamme, M. A.; Chen, K. Y.; Naumova, A. V.; Muskheli, V.; Fugate, J. A.; Dupras, S. K.; Reinecke, H.; Xu, C.; Hassanipour, M.; Police, S.; O'Sullivan, C.; Collins, L.; Chen, Y.; Minami, E.; Gill, E. A.; Ueno, S.; Yuan, C.; Gold, J.; Murry, C. E. Cardiomyocytes derived from human embryonic stem cells in pro-survival factors enhance function of infarcted rat hearts. Nat Biotechnol 2007, 25, 1015-24.
10. Singer, A. J.; Clark, R. A. Cutaneous wound healing. The New England journal of medicine 1999, 341, 738-46.
11. Martin, P. Wound healing-aiming for perfect skin regeneration. Science 1997, 276, 75-81.
12. Yang, J.; Zhang, Y.; Gautam, S.; Liu, L.; Dey, J.; Chen, W.; Mason, R. P.; Serrano, C. A.; Schug, K. A.; Tang, L. Development of aliphatic biodegradable photoluminescent polymers. Proceedings of the National Academy of Sciences of the United States of America 2009, 106, 10086-91.
13. Xie, Z.; Zhang, Y.; Liu, L.; Weng, H.; Mason, R. P.; Tang, L.; Nguyen, K. T.; Hsieh, J. T.; Yang, J Development of intrinsically photoluminescent and photostable polylactones. Advanced materials 2014, 26, 4491-6.
14. Guo, J.; Xie, Z.; Tran, R. T.; Xie, D.; Jin, D.; Bai, X.; Yang, J. Click Chemistry Plays a Dual Role in Biodegradable Polymer Design Advanced materials 2014, 26, 1906-1911.
15. Xu, L.; Zolotarskaya, O. Y.; Yeudall, W. A.; Yang, H. Click Hybridization of Immune Cells and Polyamidoamine Dendrimers. Advanced healthcare materials 2014.
16. Chow, E. K.; Ho, D. Cancer Nanomedicine: From Drug Delivery to Imaging. Science Translational Medicine 2013, 5, 216rv4.
17. Porada, C. D.; Almeida-Porada, G. Mesenchymal stem cells as therapeutics and vehicles for gene and drug delivery. Advanced drug delivery reviews 2010, 62, 1156-66.
18. Su, Y.; Xie, Z.; Kim, G. B.; Dong, C.; Yang, J. Design strategies and applications of circulating cell mediated drug delivery systems. ACS Biomaterials Science & Engineering 2015, 1, 201-217.
19. Spicer, J. D.; McDonald, B.; Cools-Lartigue, J. J.; Chow, S. C.; Giannias, B.; Kubes, P.; Ferri, L. E., Neutrophils Promote Liver Metastasis via Mac-1-Mediated Interactions with Circulating Tumor Cells, Cancer Res. 2012, 72, 3919-3927.
20. Choi, M.-R.; Stanton-Maxey, K. J.; Stanley, J. K.; Levin, C. S.; Bardhan, R.; Akin, D.; Badve, S.; Sturgis, J.; Robinson, J. P.; Bashir, R.; Halas, N. J.; Clare, S. E. A Cellular Trojan Horse for Delivery of Therapeutic Nanoparticles into Tumors. Nano Letters 2007, 7, 3759-3765.
21. Choi, M. R.; Bardhan, R.; Stanton-Maxey, K. J.; Badve, S.; Nakshatri, H.; Stantz, K. M.; Cao, N; Halas, N. J.; Clare, S. E. Delivery of nanoparticles to brain metastases of breast cancer using a cellular Trojan horse. Cancer nanotechnology 2012, 3, 47-54.
22. Madsen, S. J.; Baek, S. K.; Makkouk, A. R.; Krasieva, T.; Hirschberg, H. Macrophages as cellbased delivery systems for nanoshells in photothermal therapy. Annals of biomedical engineering 2012, 40, 507-15.
23. Mitchell, M. J.; Wayne, E.; Rana, K.; Schaffer, C. B.; King, M. R. TRAIL-coated leukocytes that kill cancer cells in the circulation. Proceedings of the National Academy of Sciences 2014, 111, 930-935.
24. Zhang, Y.; Yang, J. Design Strategies for Fluorescent Biodegradable Polymeric Biomaterials. Journal of materials chemistry B, Materials for biology and medicine 2013, 1, 132-148.
25. Xie, Z.; Zhang, Y.; Liu, L.; Weng, H.; Mason, R. P.; Tang, L.; Nguyen, K. T.; Hsieh, J. T.; Yang, J. Development of Intrinsically Photoluminescent and Photostable Polylactones. Advanced Materials 2014, 26, 4491-4496.
26. Lee, J. T.; Li, L.; Brafford, P. A.; van den Eijnden, M.; Halloran, M. B.; Sproesser, K.; Haass, N. K.; Smalley, K. S.; Tsai, J.; Bollag, G.; Herlyn, M. PLX4032, a potent inhibitor of the B-Raf V600E oncogene, selectively inhibits V600E-positive melanomas. Pigment cell & melanoma research 2010, 23, 820-7.
27. Nardin, A.; Lefebvre, M. L.; Labroquere, K.; Faure, O.; Abastado, J. P. Liposomal muramyl tripeptide phosphatidylethanolamine: Targeting and activating macrophages for adjuvant treatment of osteosarcoma. Current cancer drug targets 2006, 6, 123-33.
28. Yang, J.; Zhang, Y.; Gautam, S.; Liu, L.; Dey, J.; Chen, W.; Mason, R. P.; Serrano, C. A.; Schug, K. A.; Tang, L. Development of aliphatic biodegradable photoluminescent polymers. Proceedings of the National Academy of Sciences 2009, 106, 10086-10091.

29. Nagao, S.; Nakanishi, M.; Kutsukake, H.; Yagawa, K.; Kusumoto, S.; Shiba, T.; Tanaka, A.; Kotani, S. Macrophages are stimulated by muramyl dipeptide to induce polymorphonuclear leukocyte accumulation in the peritoneal cavities of guinea pigs. Infection and immunity 1990, 58, 536-542.
30. Wahl, S.; Wahl, L.; McCarthy, J.; Chedid, L.; Mergenhagen, S. Macrophage activation by mycobacterial water soluble compounds and synthetic muramyl dipeptide. The Journal of Immunology 1979, 122, 2226-2231.
31. Fevrier, M.; Birrien, J.; Leclerc, C.; Chedid, L. t.; Liacopoulos, P. The macrophage, target cell of the synthetic adjuvant muramyl dipeptide. European journal of immunology 1978, 8, 558-562.
32. Doane, T. L.; Chuang, C.-H.; Hill, R. J.; Burda, C. Nanoparticle ζ-Potentials. Accounts of Chemical Research 2011, 45, 317-326.
33. Leung, C. W. T.; Hong, Y.; Chen, S.; Zhao, E.; Lam, J. W. Y.; Tang, B. Z. A Photostable AIE Luminogen for Specific Mitochondrial Imaging and Tracking. Journal of the American Chemical Society 2012, 135, 62-65.
34. Daigneault, M.; Preston, J. A.; Marriott, H. M.; Whyte, M. K.; Dockrell, D. H. The identification of markers of macrophage differentiation in PMA-stimulated THP-1 cells and monocyte-derived macrophages. PloS one 2010, 5, e8668.
35. Liang, S.; Slattery, M. J.; Wagner, D.; Simon, S. I.; Dong, C. Hydrodynamic shear rate regulates melanoma-leukocyte aggregation, melanoma adhesion to the endothelium, and subsequent extravasation. Annals of biomedical engineering 2008, 36, 661-671.
36. Mittar, D.; Paramban, R.; McIntyre, C. Flow Cytometry and High-Content Imaging to Identify Markers of Monocyte-Macrophage Differentiation. 2011.
37. Dunn, G. P.; Bruce, A. T.; Ikeda, H.; Old, L. J.; Schreiber, R. D. Cancer immunoediting: from immunosurveillance to tumor escape. Nature immunology 2002, 3, 991-998.
38. Condeelis, J.; Pollard, J. W. Macrophages: Obligate Partners for Tumor Cell Migration, Invasion, and Metastasis. Cell 2006, 124, 263-266.
39. Chithrani, B. D.; Chan, W. C. W. Elucidating the Mechanism of Cellular Uptake and Removal of Protein-Coated Gold Nanoparticles of Different Sizes and Shapes. Nano Letters 2007, 7, 1542-1550.
40. Garber, K. Melanoma Drug Vindicates Targeted Approach. Science 2009, 326, 1619.
41. Comin-Anduix, B.; Chodon, T.; Sazegar, H.; Matsunaga, D.; Mock, S.; Jalil, J.; Escuin-Ordinas, H.; Chmielowski, B.; Koya, R. C.; Ribas, A. The oncogenic BRAF kinase inhibitor PLX4032/RG7204 does not affect the viability or function of human lymphocytes across a wide range of concentrations. Clinical cancer research: an official journal of the American Association for Cancer Research 2010, 16, 6040-8.
42. Urban, J. L.; Shepard, H. M.; Rothstein, J. L.; Sugarman, B. J.; Schreiber, H. Tumor necrosis factor: a potent effector molecule for tumor cell killing by activated macrophages.
Proceedings of the National Academy of Sciences 1986, 83, 5233-5237.
43. Mukherjee, K.; Parashuraman, S.; Krishnamurthy, G.; Majumdar, J.; Yadav, A.; Kumar, R.; Basu, S. K.; Mukhopadhyay, A. Diverting intracellular trafficking of Salmonella to the lysosome through activation of the late endocytic Rab7 by intracellular delivery of muramyl dipeptide. Journal of cell science 2002, 115, 3693-3701.
44. Parks, W. C. Matrix metalloproteinases in repair. Wound repair and regeneration: official publication of the Wound Healing Society [and] the European Tissue Repair Society 1999, 7, 423-32.
45. Kim, K. Y. Nanotechnology platforms and physiological challenges for cancer therapeutics. Nanomedicine: nanotechnology, biology, and medicine 2007, 3, 103-10.
46. Asian Journal of Pharmaceutical Sciences, Volume 8, Issue 3, June 2013, Pages 159-167.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:
1. A composition comprising a nanoparticle-cell conjugate, the nanoparticle-cell conjugate comprising:
   a nanoparticle comprising a therapeutic agent and being conjugated to an enzyme-sensitive degradable peptide or to a pH sensitive degradable polymer; and
   a carrier cell, wherein the nanoparticle is coupled to the carrier cell via a click chemistry reaction product between a first clickable moiety of the enzyme-sensitive degradable peptide or a first clickable moiety of the pH sensitive degradable polymer and a second clickable moiety on a surface of the carrier cell.
2. The composition of claim 1, wherein the nanoparticle is formed from a biodegradable photoluminescent polymer.
3. The composition of claim 2, wherein the biodegradable photoluminescent polymer is a block copolymer comprising:
   a first block comprising a polymer or oligomer formed from the reaction product of (i) a polycarboxylic acid or a polycarboxylic acid equivalent, (ii) a polyol, and (iii) an amino acid; and
   a second block comprising a polymer or oligomer that differs from the polymer or oligomer of the first block.
4. The composition of claim 3, wherein the polycarboxylic acid or polycarboxylic acid equivalent comprises citric acid, a citrate, or an ester of citric acid.
5. The composition of claim 3, wherein the polyol comprises an $\alpha,\omega$-n-alkane diol, a poly(ethylene glycol), or a poly(propylene glycol).
6. The composition of claim 3, wherein the amino acid comprises an alkyl-substituted alpha-amino acid.
7. The composition of claim 3, wherein the polymer or oligomer of the second block comprises a polylactone.
8. The composition of claim 3, wherein the polymer or oligomer of the second block comprises poly-DL-lactide, poly-D-lactide, poly-L-lactide, a polyglycolide, a polycaprolactone, or a mixture or copolymer of one or more of the foregoing.
9. The composition of claim 1, wherein the carrier cell is an immune cell.
10. The composition of claim 1, wherein the carrier cell is a stem cell or white blood cell.
11. The composition of claim 1, wherein the therapeutic agent comprises a targeted enzyme inhibitor.
12. The composition of 11, wherein the targeted enzyme inhibitor comprises PLX4032.
13. The composition of claim 1, wherein the therapeutic agent comprises a cytotoxic agent.
14. A method of targeted therapeutic agent delivery comprising:

disposing the composition of claim 1 into a biological environment; and delivering the nanoparticles to target cells located within the biological environment.

15. The method of claim 14, wherein, prior to disposing the composition into the biological environment, the carrier cell of the composition is isolated from human blood and functionalized with the second clickable moiety on the surface of the carrier cell.

16. The method of claim 14, wherein the target cells are cancer cells.

17. The method of claim 14, wherein the target cells form diseased, injured, or inflamed tissue.

18. The method of claim 17, wherein the carrier cell of the composition is selected from the group consisting of a monocyte, a macrophage, a T cell, a B cell, and a red blood cell.

19. The method of claim 14, wherein the biological environment is a blood stream or a blood vessel of a living organism.

20. The method of claim 14, wherein the nanoparticle of the composition is formed from a biodegradable photoluminescent polymer and the method further comprises imaging the biological environment at one or more time points using photoluminescence emitted by the biodegradable photoluminescent polymer.

\* \* \* \* \*

UNITED STATES PATENT AND TRADEMARK OFFICE
CERTIFICATE OF CORRECTION

PATENT NO. : 10,543,285 B2
APPLICATION NO. : 16/089824
DATED : January 28, 2020
INVENTOR(S) : Jian Yang et al.

It is certified that error appears in the above-identified patent and that said Letters Patent is hereby corrected as shown below:

In the Specification

Column 1, beginning at Line 19, delete "National Science Foundation"; and insert --National Institutes of Health--.

Signed and Sealed this
Third Day of May, 2022

Katherine Kelly Vidal
*Director of the United States Patent and Trademark Office*